(12) United States Patent
Chen et al.

(10) Patent No.: US 12,282,124 B2
(45) Date of Patent: *Apr. 22, 2025

(54) SYSTEM, METHOD, AND DETECTOR MODULE FOR PET IMAGING

(71) Applicant: SHANGHAI UNITED IMAGING HEALTHCARE CO., LTD., Shanghai (CN)

(72) Inventors: Ze Chen, Shanghai (CN); Ting Lu, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 314 days.

This patent is subject to a terminal disclaimer.

(21) Appl. No.: 17/655,992

(22) Filed: Mar. 22, 2022

(65) Prior Publication Data

US 2022/0214464 A1    Jul. 7, 2022

Related U.S. Application Data

(63) Continuation of application No. 15/793,959, filed on Oct. 25, 2017, now Pat. No. 11,307,313, which is a
(Continued)

(51) Int. Cl.
*G01T 1/164* (2006.01)
*A61B 5/00* (2006.01)
(Continued)

(52) U.S. Cl.
CPC .......... *G01T 1/2002* (2013.01); *A61B 5/0059* (2013.01); *A61B 6/4258* (2013.01);
(Continued)

(58) Field of Classification Search
CPC ..... A61B 6/037; G01T 1/2002; G01T 1/2004; G01T 1/2006; G01T 1/2018;
(Continued)

(56) References Cited

U.S. PATENT DOCUMENTS 7,301,153 B2    11/2007   Eriksson et al.
11,307,313 B2*   4/2022   Chen ............... G01T 1/2985
(Continued)

FOREIGN PATENT DOCUMENTS

CN   103099637 A    5/2013
EP      2383587 A2  11/2011
IT   PI20130069 A1   1/2015

OTHER PUBLICATIONS

International Search Report in PCT/CN2017/099684 mailed on May 25, 2018, 6 pages.
(Continued)

*Primary Examiner* — Carolyn A Pehlke
(74) *Attorney, Agent, or Firm* — METIS IP LLC

(57) ABSTRACT

The present disclosure relates to a system for PET imaging. The system may include a detector module and an electronics module. The detector module may include a scintillator array having N rows of scintillators arranged in a first direction and M columns of scintillators arranged in a second direction, a first set of photosensors coupled to the scintillator array and extending in the second direction, and a second set of photosensors coupled to the scintillator array and extending in the first direction. The electronics module may detect a first set of electrical signals generated by the first set of photosensors and a second set of electrical signals generated by the second set of photosensors, and identify a scintillator within the scintillator array that has interacted with an impinging radiation ray relating to an electrical signal of the first set of electrical signals or the second set of electrical signals.

20 Claims, 15 Drawing Sheets

Related U.S. Application Data continuation of application No. PCT/CN2017/099684, filed on Aug. 30, 2017.

(51) Int. Cl.
| | | |
|---|---|---|
| *A61B 6/42* | (2024.01) | |
| *G01N 21/64* | (2006.01) | |
| *G01T 1/20* | (2006.01) | |
| *G01T 1/29* | (2006.01) | |

(52) U.S. Cl.
CPC ....... *G01N 21/6408* (2013.01); *G01T 1/1642* (2013.01); *G01T 1/1644* (2013.01); *G01T 1/2985* (2013.01)

(58) Field of Classification Search
CPC ............. G01T 1/20181; G01T 1/20182; G01T 1/1642; G01T 1/1644; G01T 1/2985
See application file for complete search history.

(56) References Cited

U.S. PATENT DOCUMENTS

| | | |
|---|---|---|
| 2004/0195512 A1 | 10/2004 | Crosetto |
| 2005/0006589 A1 | 1/2005 | Joung et al. |
| 2005/0023474 A1 | 2/2005 | Persyk et al. |
| 2006/0197022 A1 | 9/2006 | Burr et al. |
| 2010/0219345 A1 | 9/2010 | Franch et al. |
| 2013/0153776 A1 | 6/2013 | Wieczorek et al. |
| 2013/0256536 A1 | 10/2013 | Kim |
| 2014/0084170 A1 | 3/2014 | Wieczorek et al. |
| 2014/0246594 A1 | 9/2014 | Pichler et al. |
| 2015/0028218 A1 | 1/2015 | Kataoka et al. |
| 2015/0177390 A1 | 6/2015 | Mattson et al. |
| 2015/0192685 A1 | 7/2015 | Griesmer et al. |
| 2016/0097866 A1 | 4/2016 | Williams |
| 2016/0154121 A1 | 6/2016 | Luhta et al. |
| 2016/0274249 A1 | 9/2016 | Vogtmeier et al. |
| 2017/0234990 A1 | 8/2017 | Sowards-Emmerd et al. |
| 2018/0059266 A1 | 3/2018 | Berker et al. |
| 2018/0196144 A1 | 7/2018 | Teshigawara |

OTHER PUBLICATIONS

Written Opinion in PCT/CN2017/099684 mailed on May 25, 2018, 4 pages.

First Office Action in Chinese Application No. 201711229753.X mailed on Mar. 12, 2020, 13 pages.

First Office Action in Chinese Application No. 201711229755.9 mailed on Mar. 30, 2021, 13 pages.

Ding, Lili et al., Nuclear Technology In Biomedicine, China University of science and Technology Press, 2010, 6 pages.

Jin, Yongjie, Nuclear Medical Instruments And Methods, Harbin Engineering University Press, 2010, 6 pages.

The Second Office Action in Chinese Application No. 201711229755.9 mailed on Sep. 1, 2021, 15 pages.

Sun, Xishan et al., Energy and Timing Measurement with Time-Based Detector Readout for PET Applications: Principle and Validation with Discrete Circuit Components, Nuclear Instruments and Methods in Physics, 2011, 23 pages.

* cited by examiner

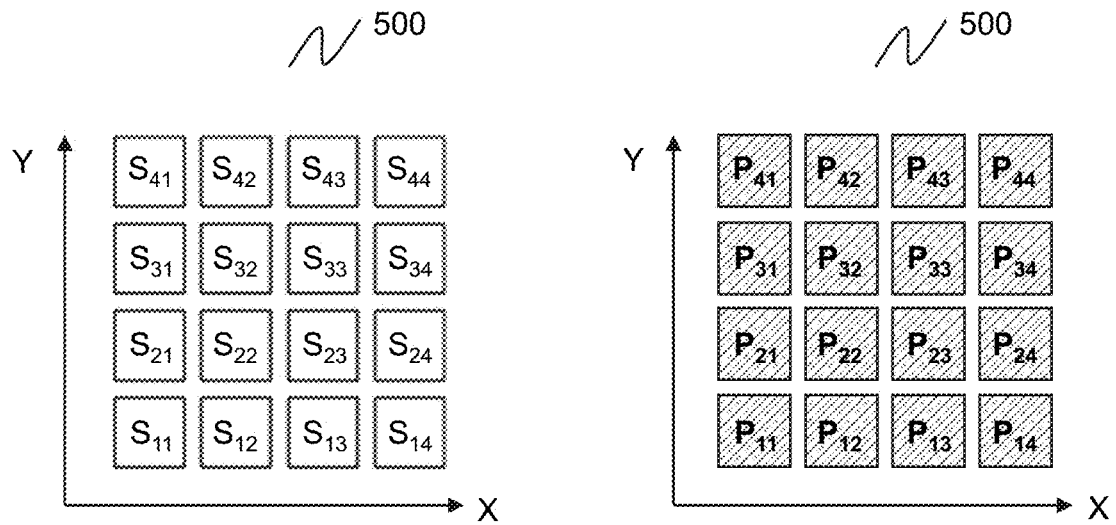
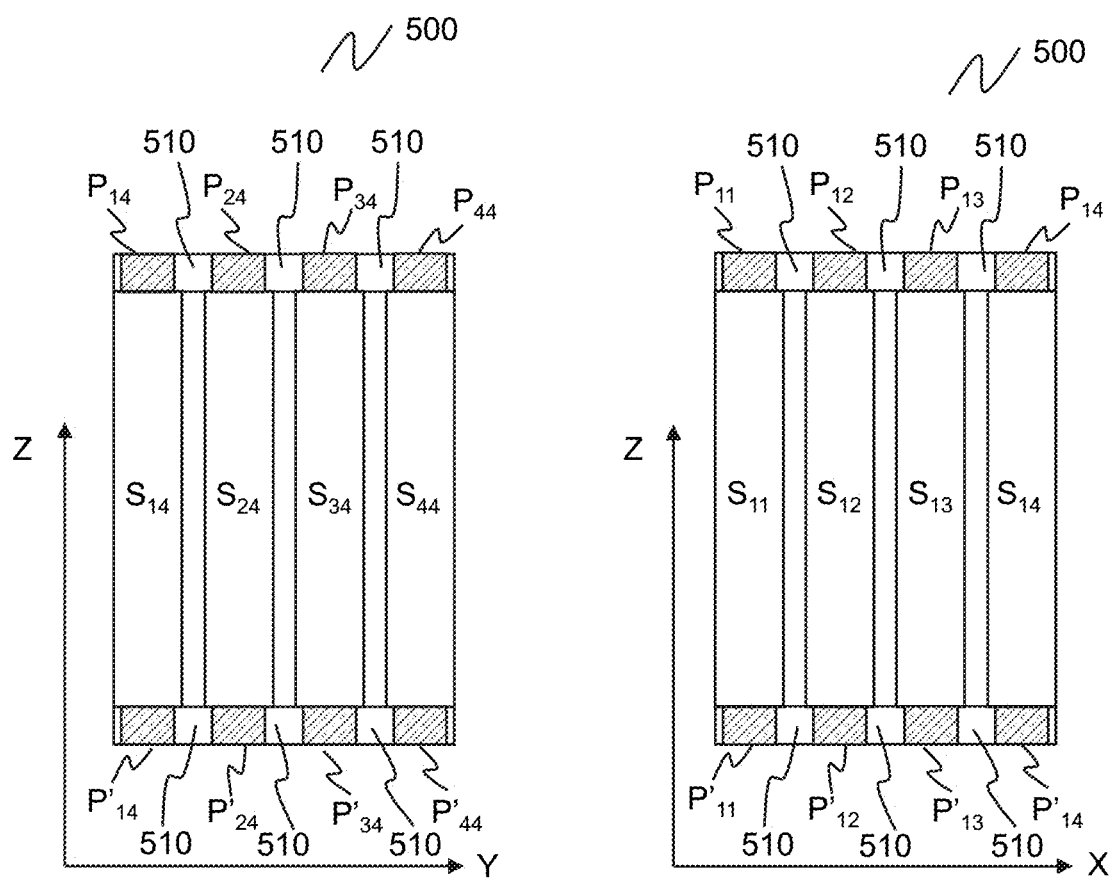
FIG. 5A
FIG. 5B
FIG. 5C
FIG. 5D

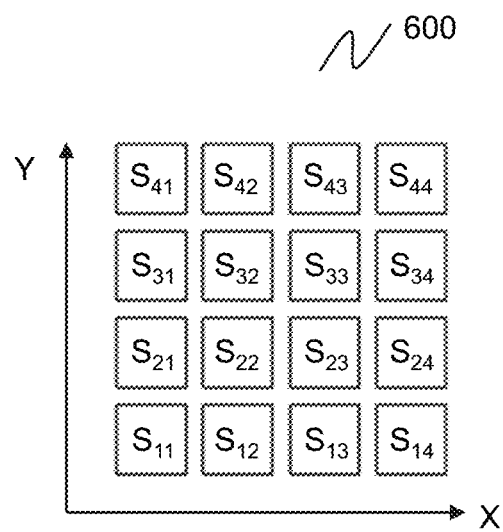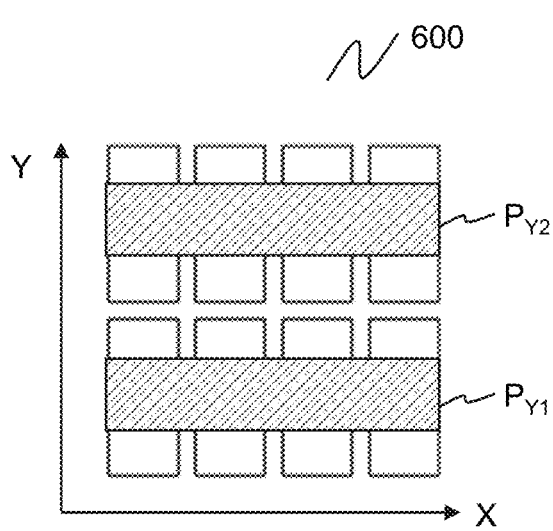
FIG. 7A    FIG. 7B
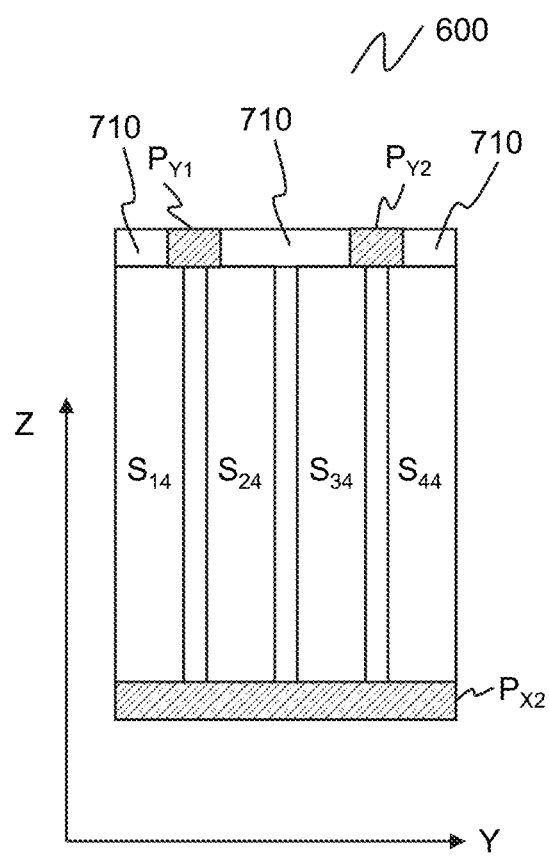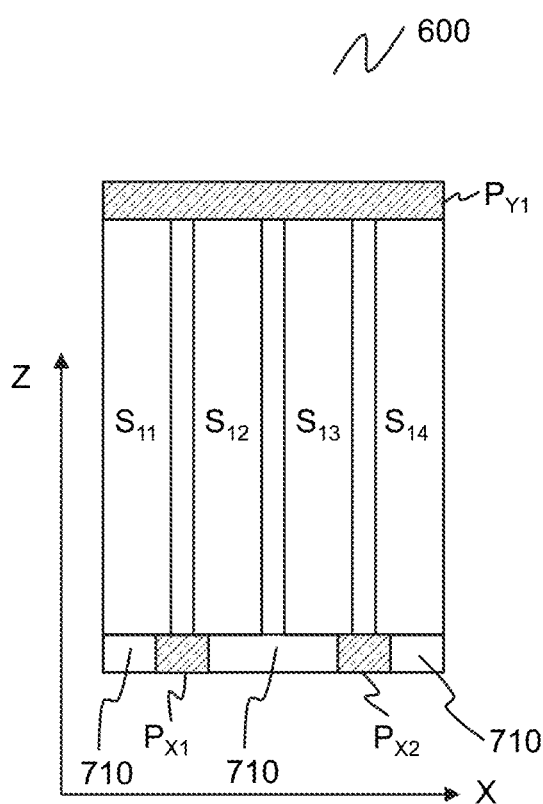
FIG. 7C    FIG. 7D

SYSTEM, METHOD, AND DETECTOR MODULE FOR PET IMAGING

CROSS-REFERENCE TO RELATED APPLICATIONS

This present application is a continuation of U.S. application Ser. No. 15/793,959, filed on Oct. 25, 2017, which is a continuation of International Application No. PCT/CN2017/099684, filed on Aug. 30, 2017, the contents of each of which are hereby incorporated by reference.

TECHNICAL FIELD

The present disclosure generally relates to optical detection, and more particularly, a system, method, and detector module for PET imaging.

BACKGROUND

Generally, positron emission tomography (PET) detector modules have been set in various medical devices such as, positron emission tomography devices, positron emission tomography-computed tomography (PET-CT) devices, and positron emission tomography-magnetic resonance imaging (PET-MRI) devices, in which PET technologies are applied. PET detector modules are used to receive radiation rays (e.g., γ rays) generated from a patient's body and to provide information relating to the locations where photons are excited by the radiation rays. PET detector modules may generate electrical signals based on the radiation rays, and then the electrical signals may be detected and used to reconstruct an image.

A PET detector module may include a scintillator array, and a plurality of photosensors (e.g., silicon photomultipliers (SiPM)) optically coupled to the scintillator array. The photosensors may have various configurations. With more photosensors, the detection performance of the medical devices may be relatively high, but the cost and complexity of the medical devices may be relatively high. With fewer photosensors, the detection performance of the medical devices may be relatively low, but the cost and complexity of the medical devices may be relatively low. It is desirable to seek a balance between maintaining a relatively high performance and lowering the cost and complexity of the medical devices.

SUMMARY

One aspect of the present disclosure relates to a PET system for imaging. The PET system may include a detector module and an electronics module. The detector module may be configured to receive radiation rays and generate a plurality of light signals in response to the received radiation rays. The detector module may include a scintillator array having N rows of scintillators arranged in a first direction and M columns of scintillators arranged in a second direction, a first set of photosensors optically coupled to a first surface of the scintillator array and extending in the second direction, and a second set of photosensors optically coupled to a second surface of the scintillator array and extending in the first direction. The electronics module may be coupled to the first set of photosensors and the second set of photosensors. The electronics module may configured to detect a first set of electrical signals generated by the first set of photosensors and a second set of electrical signals generated by the second set of photosensors, and identify a scintillator within the scintillator array that has interacted with an impinging radiation ray relating to an electrical signal of the first set of electrical signals or the second set of electrical signals.

Another aspect of the present disclosure relates to a method for PET imaging. The method may include one or more of the following operations. A plurality of radiation rays may be detected using a scintillator array, wherein the scintillator array may include N rows of scintillators arranged in a first direction and M columns of scintillators arranged in a second direction. A first set of electrical signals may be generated based on the plurality of radiation rays using a first set of photosensors, wherein the first set of photosensors may be optically coupled to a first surface of the scintillator array and extending in the second direction. A second set of electrical signals may be generated based on the plurality of radiation rays using a second set of photosensors, wherein the second set of photosensors may be optically coupled to a second surface of the scintillator array and extending in the first direction. A scintillator within the scintillator array that has interacted with an impinging radiation ray relating to an electrical signal of the first set of electrical signals or the second set of electrical signals may be identified using an electronics module.

A further aspect of the present disclosure relates to a detector module. The detector module may be configured to receive radiation rays and generate a plurality of light signals in response to the received radiation rays. The detector module may include a scintillator array having N rows of scintillators arranged in a first direction and M columns of scintillators arranged in a second direction, a first set of photosensors optically coupled to a first surface of the scintillator array and extending in the second direction, and a second set of photosensors optically coupled to a second surface of the scintillator array and extending in the first direction.

In some embodiments, the first set of photosensors or the second set of photosensors may include at least one silicon photomultiplier (SiPM).

In some embodiments, the PET system may further include a gantry with a detection region for receiving a subject to be scanned, wherein the first surface or the second surface of the scintillator array may face the detection region.

In some embodiments, the first direction may be approximately perpendicular to the second direction.

In some embodiments, at least one of the first set of photosensors may be coupled to two rows of scintillators of the N rows, and at least one of the second set of photosensors may be coupled to two columns of scintillators of the M columns.

In some embodiments, an area of a first photosensor of the first set of photosensors may be less than a sum of areas of the two rows of scintillators to which the first photosensor is coupled.

In some embodiments, an area of a second photosensor of the second set of photosensors may be less than a sum of areas of the two columns of scintillators to which the second photosensor is coupled.

In some embodiments, a number of the first set of photosensors may be no less than a half of N, and a number of the second set of photosensors may be no less than a half of M.

In some embodiments, N may equal M, or N may be different from M.

In some embodiments, the electronics module may be further configured to determine a depth of interaction of the impinging radiation ray in the identified scintillator.

In some embodiments, the electronics module may include a plurality of analog-to-digital converters (ADC) configured to digitize the first set of electrical signals and the second set of electrical signals, and a position decoding unit configured to identify, based on the digitized first set of electrical signals and the digitized second set of electrical signals, the scintillator within the scintillator array that has interacted with the impinging radiation ray.

In some embodiments, the position decoding unit may be further configured to determine a depth of interaction of the impinging radiation ray.

In some embodiments, the electronics module may further include a lower limit detection (LLD) circuit or a constant fraction discriminator (CFD) circuit, and a time-to-digital converter (TDC) configured to determine an interaction time when the impinging radiation ray interacts with the identified scintillator.

In some embodiments, the electronics module may further include a time correction unit configured to correct the interaction time based on the depth of interaction of the impinging radiation ray.

In some embodiments, the PET system may further include a processing module configured to reconstruct an image based on the first set of electrical signals generated by the first set of photosensors and the second set of electrical signals generated by the second set of photosensors.

In some embodiments, the identification of a scintillator within the scintillator array that has interacted with an impinging radiation ray relating to an electrical signal of the first set of electrical signals or the second set of electrical signals may include one or more of the following operations. A first position of the impinging radiation ray that has interacted with the scintillator array in the first direction may be determined based on the first set of electrical signals using an algorithm. A second position of the impinging radiation ray that has interacted with the scintillator array in the second direction may be determined based on the second set of electrical signals using the algorithm. The scintillator within the scintillator array that has interacted with the impinging radiation ray may be identified based on the first position and the second position.

In some embodiments, the method may further include one or more of the following operations. A depth of interaction of the impinging radiation ray in the identified scintillator may be identified based on the first set of electrical signals and the second set of electrical signals using the algorithm.

In some embodiments, the method may further include one or more of the following operations. An interaction time when the impinging radiation ray interacts with the identified scintillator may be determined using a time-to-digital converter (TDC).

In some embodiments, the method may further include one or more of the following operations. The interaction time may be corrected based on the depth of interaction of the impinging radiation ray in the identified scintillator.

In some embodiments, the first direction may correspond to an X axis direction, the first position of the impinging radiation ray may correspond to a position in the X axis direction, and the determination the first position of the impinging radiation ray that has interacted with the scintillator array in the first direction may include one or more of the following operations. A position of a first photosensor that generates an electrical signal with maximum energy of the first set of electrical signals in the X axis direction may be designated as the first position, or a position of an energy centroid of the first set of electrical signals in the X axis direction may be designated as the first position.

In some embodiments, the second direction may correspond to a Y axis direction, the second position of the impinging radiation ray may correspond to a position in the Y axis direction, and the determination of the second position of the impinging radiation ray that has interacted with the scintillator array in the second direction may include one or more of the following operations. A position of a second photosensor that generates an electrical signal with maximum energy of the second set of electrical signals in the Y axis direction may be designated as the second position, or a position of an energy centroid of the second set of electrical signals in the Y axis direction may be designated as the second position.

In some embodiments, the depth of interaction of the impinging radiation ray in the identified scintillator may correspond to a position in a Z axis direction that is perpendicular to the first direction and the second direction, and the identification of the depth of interaction of the impinging radiation ray in the identified scintillator may include one or more of the following operations. A proportional distribution coefficient may be determined based on a ratio of first energy relating to the first set of electrical signals to second energy relating to the first set of electrical signals and the second set of electrical signals. The depth of interaction of the impinging radiation ray may be determined based on the proportional distribution coefficient.

In some embodiments, the first energy may relate to a first sum of the first set of electrical signals, the second energy may relate to a second sum of the first set of electrical signals and the second set of electrical signals, and the first set of electrical signals and the second set of electrical signals may be converted by at least one analog-to-digital converter and processed by a position decoding unit.

In some embodiments, the impinging radiation ray may interact with the scintillator array from the first surface of the scintillator array, and the determination of an interaction time may include one or more of the following operations. A third sum of the first set of electrical signals may be determined. The interaction time may be determined based on the third sum of the first set of electrical signals using a lower limit detection (LLD) circuit, a constant fraction discriminator (CFD) circuit, and/or a time-to-digital converter (TDC).

In some embodiments, the impinging radiation ray may interact with the scintillator array from the second surface of the scintillator array, and the determination of an interaction time may include one or more of the following operations. A fourth sum of the second set of electrical signals may be determined. The interaction time may be determined based on the fourth sum of the second set of electrical signals using a lower limit detection (LLD) circuit, or a constant fraction discriminator (CFD) circuit, and a time-to-digital converter (TDC).

In some embodiments, the scintillator array may further include S rows of blocks arranged in the first direction and T columns of blocks arranged in the second direction, wherein each block may include N rows of scintillators arranged in the first direction and M columns of scintillators arranged in the second direction, and the method may further include one or more of the following operations. A sum of S electrical signals generated by S photosensors that are optically coupled to the first surface of the scintillator array and arranged in a same column of the T columns of blocks may be designated as one of the first set of electrical signals. A sum of T electrical signals generated by T photosensors that are optically coupled to the second surface of the scintillator array and arranged in a same row of the S rows of blocks may be designated as one of the second set of electrical signals.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 5A is a schematic diagram illustrating a top view of a 4×4 scintillator array of an exemplary detector module according to some embodiments of the present disclosure;

FIG. 5B is a schematic diagram illustrating a top view of a 4×4 first photosensor array of an exemplary detector module according to some embodiments of the present disclosure;

FIG. 5C is a schematic diagram illustrating a right view of an exemplary detector module according to some embodiments of the present disclosure;

FIG. 5D is a schematic diagram illustrating a front view of an exemplary detector module according to some embodiments of the present disclosure;

FIG. 7A is a schematic diagram illustrating a top view of a 4×4 scintillator array of an exemplary detector module according to some embodiments of the present disclosure;

FIG. 7B is a schematic diagram illustrating a top view of a 2×1 first photosensor array of an exemplary detector module according to some embodiments of the present disclosure;

FIG. 7C is a schematic diagram illustrating a right view of an exemplary detector module according to some embodiments of the present disclosure;

FIG. 7D is a schematic diagram illustrating a front view of an exemplary detector module according to some embodiments of the present disclosure;

DETAILED DESCRIPTION

Figure 1:
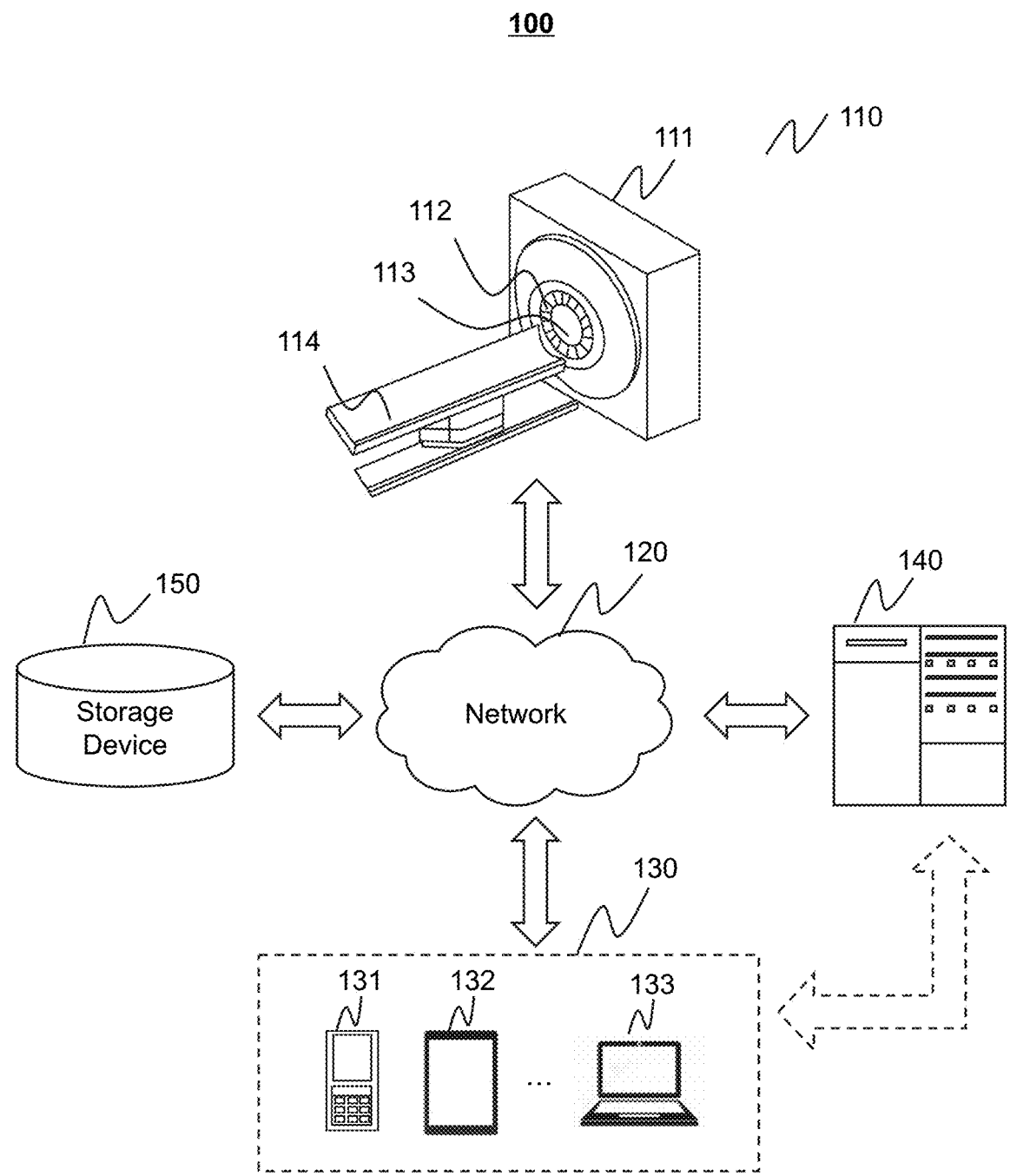
FIG. 1 is a schematic diagram illustrating an exemplary PET imaging system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by another expression if they achieve the same purpose.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

For illustration purposes, the following description is provided with reference to a PET detector module. It is understood that this is not intended to limit the scope of the present disclosure. For persons having ordinary skills in the art, a certain amount of variations, changes and/or modifications may be deducted under the guidance of the present disclosure. Those variations, changes and/or modifications do not depart from the scope of the present disclosure.

FIG. 1 is a schematic diagram illustrating an exemplary PET imaging system 100 according to some embodiments of the present disclosure. As shown, the PET imaging system 100 may include a scanner 110, a network 120, one or more terminals 130, a processing engine 140, and a storage device 150. The components in the imaging system 100 may be connected in one or more of variable ways. Merely by way of example, as illustrated in FIG. 1, the scanner 110 may be connected to the processing engine 140 through the network 120. As another example, the scanner 110 may be connected to the processing engine 140 directly. As a further example, the storage device 150 may be connected to the processing engine 140 directly or through the network 120. As still a further example, a terminal 130 may be connected to the processing engine 140 directly or through the network 120.

The scanner 110 may scan an object, and/or generate a plurality of data relating to the object. In some embodiments, the scanner 110 may be a medical imaging device, for example, a PET device, a PET-CT device, a PET-MRI device, etc. The scanner 110 may include a gantry 111, a detector assembly 112, a detection region 113, and a table 114. A subject may be placed on the table 114 for scanning. In the present disclosure, "object" and "subject" are used interchangeably. The detector assembly 112 may detect radiation events (e.g., gamma photons) emitted from the detection region 113. In some embodiments, the detector assembly 112 may include one or more detector modules. The detector modules may be implemented in any suitable configuration, for example, a ring, a rectangle, or an array. In some embodiments, a detector module may include one or more crystal elements and/or one or more photomultipliers (e.g., silicon photomultiplier (SiPM)) (not shown). In some embodiments, a SiPM as employed in the present disclosure may be a single-channel SiPM or a multi-channel SiPM. The table 114 may facilitate the positioning of a subject in the detection region 113.

The network 120 may include any suitable network that can facilitate exchange of information and/or data for the PET imaging system 100. In some embodiments, one or more components of the PET imaging system 100 (e.g., the scanner 110, the terminal 130, the processing engine 140, the storage device 150, etc.) may communicate information and/or data with one or more other components of the PET imaging system 100 via the network 120. For example, the processing engine 140 may obtain image data from the scanner 110 via the network 120. As another example, the processing engine 140 may obtain user instructions from the terminal 130 via the network 120. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the PET imaging system 100 may be connected to the network 120 to exchange data and/or information.

The terminal(s) 130 may include a mobile device 131, a tablet computer 132, a laptop computer 133, or the like, or any combination thereof. In some embodiments, the mobile device 131 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footgear, eyeglasses, a helmet, a watch, clothing, a backpack, a smart accessory, or the like, or any combination thereof. In some embodiments, the mobile device may include a mobile phone, a personal digital assistance (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 130 may be part of the processing engine 140.

The processing engine 140 may process data and/or information obtained from the scanner 110, the terminal(s) 130, and/or the storage device 150. For example, the processing engine 140 may process image data and reconstruct an image based on the image data. In some embodiments, the processing engine 140 may be a single server or a server group. The server group may be centralized or distributed. In some embodiments, the processing engine 140 may be local or remote. For example, the processing engine 140 may access information and/or data stored in the scanner 110, the terminal(s) 130, and/or the storage device 150 via the network 120. As another example, the processing engine 140 may be directly connected to the scanner 110, the terminal(s) 130 and/or the storage device 150 to access stored information and/or data. In some embodiments, the processing engine 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing engine 140 may be implemented by a computing device. In some embodiments, the processing engine 140, or a portion of the processing engine 140 may be integrated into the scanner 110.

The storage device 150 may store data, instructions, and/or any other information. In some embodiments, the storage device 150 may store data obtained from the terminal(s) 130 and/or the processing engine 140. In some embodiments, the storage device 150 may store data and/or instructions that the processing engine 140 may execute or use to perform exemplary methods described in the present disclosure. In some embodiments, the storage device 150 may include a mass storage device, a removable storage device, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more other components in the PET imaging system 100 (e.g., the processing engine 140, the terminal(s) 130, etc.). One or more components of the PET imaging system 100 may access the data or instructions stored in the storage device 150 via the network 120. In some embodiments, the storage device 150 may be directly connected to or communicate with one or more other components in the PET imaging system 100 (e.g., the processing engine 140, the terminal(s) 130, etc.). In some embodiments, the storage device 150 may be part of the processing engine 140.

Figure 2A:
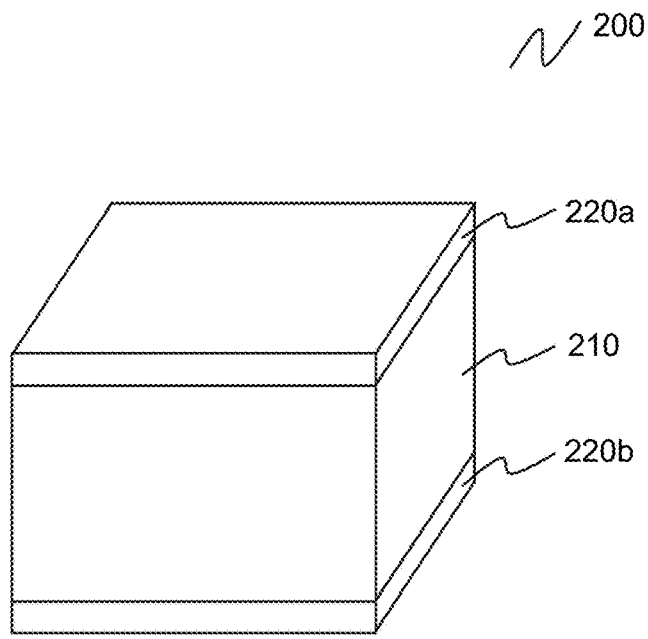
FIGS. 2A-2C are schematic diagrams illustrating an exemplary detector module according to some embodiments of the present disclosure.
Figure 2B:
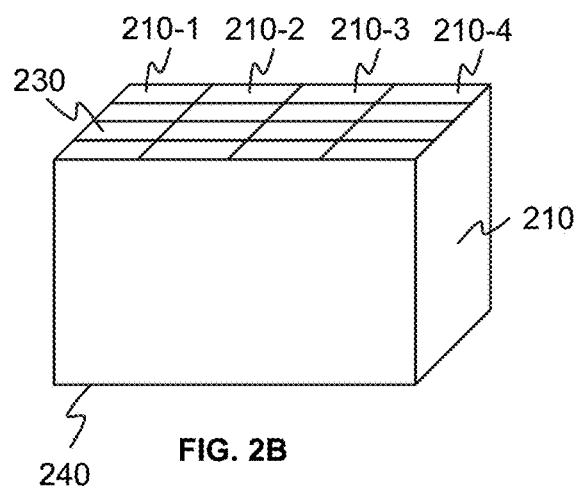
Figure 2C:
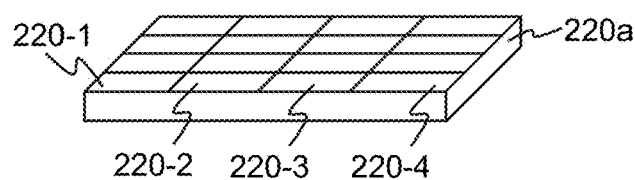

FIGS. 2A-2C are schematic diagrams illustrating an exemplary detector module 200 according to some embodiments of the present disclosure. As described in FIG. 1, the detector assembly 112 may include one or more detector modules. A detector module 200 may include one or more crystal elements (e.g., the scintillator crystal array 210) and one or more photosensor arrays 220 (e.g., the first photosensor array 220a, the second photosensor array 220b).

As shown in FIG. 2A, the crystal elements may be configured as a scintillator crystal array 210 (also referred to as scintillator array 210). The scintillator array 210 may include one or more scintillators (e.g., the scintillator 210-1, the scintillator 210-2, the scintillator 210-3, the scintillator 210-4, etc., as illustrated in FIG. 2B). A scintillator may scintillate when a radiation ray (e.g., γ ray) photon collides (or impinges) the scintillator. The scintillator may absorb the energy of the radiation ray (e.g., γ ray) photon, and convert the absorbed energy into light. In some embodiments, the scintillator array 210 may include N rows of scintillators and M columns of scintillators. The row count N may be an integer larger than 0. The column count M may be an integer larger than 0. In some embodiments, N may be equal to M. In some embodiments, N may be different from M. In some embodiments, the N rows of scintillators may be arranged parallel to a first direction (e.g., the X axis direction in FIG. 3A or FIG. 6A) but approximately perpendicular to a second direction (e.g., the Y axis direction in FIG. 3A or FIG. 6A), while the M columns of scintillators may be arranged parallel to the second direction but approximately perpendicular to the first direction. In some embodiments, the second direction may be approximately perpendicular to the first direction. In some embodiments, an angle between the first direction and the second direction may be different from 90°. FIG. 2B illustrates an exemplary 4×4 scintillator array. The scintillator array 210 may have a first surface 230 and a second surface 240 opposite to the first surface 230. The first surface 230 may be a common face formed by one end of all the scintillators (e.g., a top surface) in the scintillator array 210. The second surface 240 may be a common face formed by another end of all the scintillators (e.g., a bottom surface) in the scintillator array 210. In some embodiments, the first surface 230 or the second surface 240 may face the detection region 113.

A photosensor array 220 (e.g., the first photosensor array 220a, the second photosensor array 220b) may include one or more photosensors (e.g., the photosensor 220-1, the photosensor 220-2, the photosensor 220-3, the photosensor 220-4, etc. as illustrated in FIG. 2C). In some embodiments, the photosensor array 220 may be configured to face the detection region 113. If the photosensor array 220 is configured to face the detection region 113, the photosensor array 220 may not block radiation rays from reaching the scintillator array 210. If the photosensor array 220 is configured to face the detection region 113, the radiation rays may slightly attenuate before reaching the scintillator array 210. However, the attenuation of the radiation rays may not affect the detection result of the detector assembly 112. A photosensor may convert a light signal (e.g., the light output from a scintillator) to an electrical signal. In some embodiments, a photosensor may be a photomultiplier tube (PMT), a silicon photomultiplier (SiPM), etc. The photosensor array (s) 220 may be optically coupled to the scintillator array 210. As used herein, a photosensor or a photosensor array being optically coupled to a scintillator or a scintillator array may indicate that an optical signal may transport between the scintillator or the scintillator array and the photosensor or the photosensor array. For example, the first photosensor array 220a (also referred to as a first set of photosensors) may be arranged on the first surface 230 of the scintillator array 210. As another example, the second photosensor array 220b (also referred to as a second set of photosensors) may be arranged on the second surface 240 of the scintillator array 210. In some embodiments, both the first photosensor array 220a and the second photosensor array 220b may be optically coupled to the scintillator array 210. In some embodiments, only the first photosensor array 220a or the second photosensor array 220b may be optically coupled to the scintillator array 210. In some embodiments, a photosensor array 220 may include N' rows of photosensors and M' columns of photosensors. N' may be an integer larger than 0 but no larger than N. M' may be an integer larger than 0 but no larger than M.

In some embodiments, a photosensor may be optically coupled to only one scintillator (see FIGS. 5A-5D). Accordingly, the number of photosensors in the N'×M' photosensor array 220 may be the same as that of scintillators in the N×M scintillator array 210. As illustrated, a 4×4 photosensor array (see FIG. 2C) may be optically coupled to a 4×4 scintillator array (see FIG. 2B). For example, the photosensor 220-1 may be optically coupled to the scintillator 210-1, the photosensor 220-2 may be optically coupled to the scintillator 210-2, the photosensor 220-3 may be optically coupled to the scintillator 210-3, the photosensor 220-4 may be optically coupled to the scintillator 210-4, and so on. In this case, it may be unnecessary that both the first photosensor array 220a and the second photosensor array 220b are optically coupled to the scintillator array 210. In this case, as a photosensor is optically coupled to an identified scintillator, a hit position where a radiation ray (e.g., γ ray) photon collides the scintillator array 210 may be identified (i.e., a scintillator within the scintillator array 210 that has interacted with an impinging radiation ray may be identified) based on the electrical signals that the photosensor detects. Therefore, the first photosensor array 220a or the second photosensor array 220b may be sufficient to detect a light output from the scintillator array 210.

In some embodiments, the size (or area) of the entry surface of a photosensor may be the same as the size (or area) of the exit surface of an optically coupled scintillator. As used herein, an entry surface of a photosensor (or photosensor array) may refer to a surface of the photosensor (or photosensor array) where an optical signal (e.g., an optical signal from the optically coupled scintillator (or scintillator array)) enters the photosensor. As used herein, an exit surface of a scintillator (or scintillator array) may refer to a surface of the scintillator (or scintillator array) where an optical signal exits the scintillator (or scintillator array). In some embodiments, the size (or area) of the entry surface of a photosensor may be different from (e.g., smaller or larger than) the size (or area) of the exit surface of an optically coupled scintillator. For example, the size (or area) of the entry surface of a photosensor may be a fraction (e.g., ¾, ⅔, ½, etc.) of that of an exit surface of an optically coupled scintillator.

In some embodiments, a photosensor may be optically coupled to two or more scintillators (see FIGS. 3A and 3B, FIGS. 4A-4D, FIGS. 6A and 6B, FIGS. 7A-7D, and FIGS. 8A-8E). In some embodiments, a photosensor may be optically coupled to at least two scintillators in two adjacent rows of the N rows of a scintillator array. In some embodiments, a photosensor may be optically coupled to at least two scintillators in two adjacent columns of the M columns of a scintillator array. In some embodiments, at least one of the first set of photosensors (or the first photosensor array 220a) may be coupled to two rows of scintillators of the N rows. In some embodiments, an area of a first photosensor of the first set of photosensors may be less than a sum of areas of the two rows of scintillators to which the first photosensor is coupled. In some embodiments, at least one of the second set of photosensors (or the second photosensor array 220b) may be coupled to two columns of scintillators of the M columns. In some embodiments, an area of a second photosensor of the second set of photosensors may be less than a sum of areas of the two columns of scintillators to which the second photosensor is coupled. Accordingly, the number of photosensors in the N'×M' photosensor array 220 may be less than that of scintillators in the N×M scintillator array 210. For example, a photosensor may be optically coupled to i (e.g., 2, 3, 4, etc.) scintillators in a same row or column. As another example, a photosensor may be optically coupled to a sub-array of i×j (e.g., 2×2, 2×3, 2×4, etc.) scintillators in adjacent rows or columns. In some embodiments, in the photosensor array 220 (e.g., the first photosensor array 220a, the second photosensor array 220b), different photosensors may be optically coupled to different numbers of scintillators. Merely by way of example, a photosensor A may be optically coupled to two scintillators, a photosensor B may be optically coupled to three scintillators, a photosensor C may be optically coupled to four scintillators, and the scintillators to which the photosensors are coupled may be arranged in different (or the same) rows or columns. In some embodiments, the size (or area) of the entry surface of a photosensor may be the same as a sum of the sizes (or areas) of the exit surfaces of the scintillators to which the photosensor is optically coupled. In some embodiments, the size (or area) of the entry surface of a photosensor may be different from (e.g., smaller or larger than) a sum of the sizes (or areas) of the exit surfaces of the scintillators to which the photosensor is coupled. For example, the size (or area) of the entry surface of a photosensor may be a fraction (e.g., ¾, ⅔, ½, etc.) of a sum of the sizes (or areas) of the exit surfaces of the scintillators to which the photosensor is optically coupled.

In some embodiments, two adjacent photosensors in the first photosensor array 220a or the second photosensor array 220b may be arranged apart by a certain distance. The distance between two adjacent photosensors may be no less than the width of a scintillator. In some embodiments, the number of the photosensors in the first photosensor array 220a (or the first set of photosensors) or the second photosensor array 220b (or the second set of photosensors) may be no less than a half of N, the row count of scintillators of the optically coupled scintilator array 210. In some embodiments, the number of the photosensors in the first photosensor array 220a (or the first set of photosensors) or the second photosensor array 220b (or the second set of photosensors) may be no less than a half of M, the column count of scintillators of the optically coupled scintilator array 210.

In some embodiments, if both the first photosensor array 220a and the second photosensor array 220b are optically coupled to the scintillator array 210, the number (or area) of photosensors in the first photosensor array 220a and the number (or area) of the second photosensor array 220b may be the same or different. In some embodiments, if both the first photosensor array 220a and the second photosensor array 220b are optically coupled to the scintillator array 210, the arrangement of photosensors in the first photosensor array 220a and the second photosensor array 220b may be different. For example, photosensors in the first photosensor array 220a may be arranged in the first direction, while photosensors in the second photosensor array 220b may be arranged in the second direction, and vice versa (see FIGS. 3A and 3B, FIGS. 4A-4D, FIGS. 6A and 6B, FIGS. 7A-7D, and FIGS. 8A-8E).

It should be noted that the above description of the detector module 200 is merely provided for the purpose of illustration, and not intended to limit the scope of the present disclosure. For persons having ordinary skills in the art, multiple variations and modifications may be made to the detector module 200 under the teachings of the present disclosure. However, those variations and modifications do not depart from the scope of the present disclosure. For example, one or more light guides may be configured between the scintillator array 210 and the photosensor array 220 to facilitate light transmission from the scintillator array 210 to the photosensor array 220.

Figure 3A:
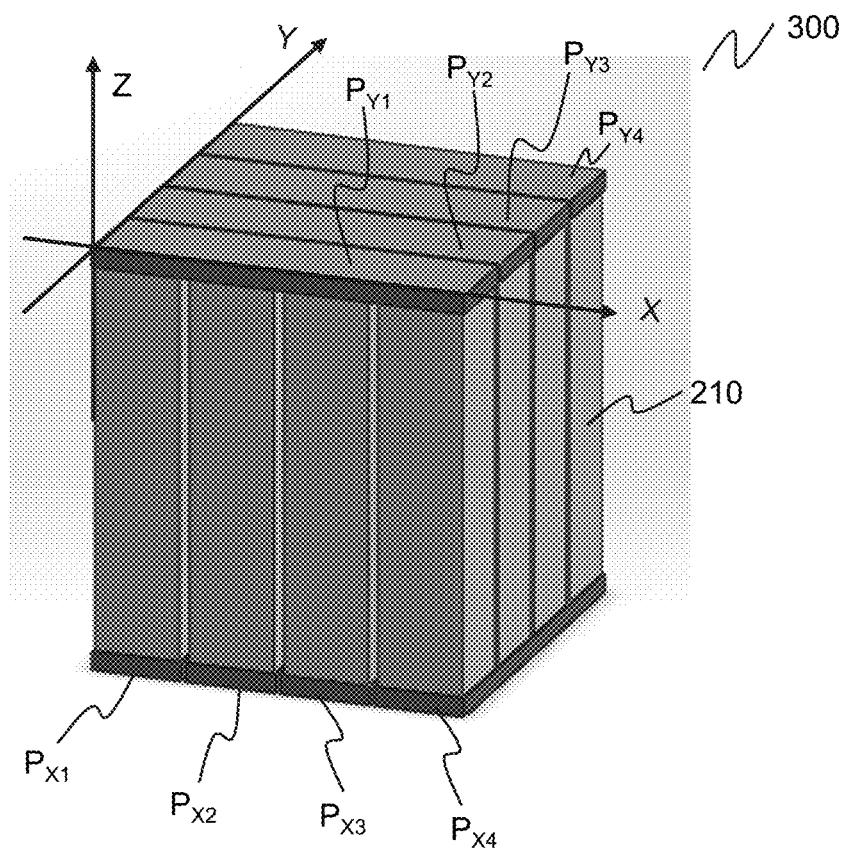
FIG. 3A is a schematic diagram illustrating an exemplary detector module according to some embodiments of the present disclosure.

FIG. 3A is a schematic diagram illustrating an exemplary detector module 300 according to some embodiments of the present disclosure. The detector module 300 may include a 4×4 scintillator array 210, four photosensors (e.g., SiPM) within the first photosensor array 220a, and four photosensors (e.g., SiPM) within the second photosensor array 220b.

The 4×4 scintillator array 210 may have a top surface and a bottom surface both in the X-Y plane. The top surface may face the detection region 113. The 16 scintillators within the 4×4 scintillator array 210 may be arranged parallel to the Z axis direction. In some embodiments, the Z axis may point to a radial direction of the detection region 113. The 16 scintillators within the 4×4 scintillator array 210 may have the same height. Four scintillators in each row may be arranged in the X axis direction. Four scintillators in each column may be arranged in the Y axis direction. In some embodiments, the axial direction of the detection region 113 may be along the X axis, and the Y axis may be perpendicular to the X axis and the Z axis. In some embodiments, the axial direction of the detection region 113 may be along the Y axis, and the X axis may be perpendicular to the Y axis and the Z axis.

The first photosensor array 220a may be optically coupled to the 4×4 scintillator array 210 and arranged on the top surface of the scintillator array 210. The first photosensor array 220a may include four photosensors, i.e., the photosensor $P_{Y1}$, the photosensor $P_{Y2}$, the photosensor $P_{Y3}$, and the photosensor $P_{Y4}$. The four photosensors $P_{Y1}$, $P_{Y2}$, $P_{Y3}$, and $P_{Y4}$ may be arranged parallel to the X axis direction. The second photosensor array 220b may be optically coupled to the 4×4 scintillator array 210 and arranged on the bottom surface of the scintillator array 210. The second photosensor array 220b may include four photosensors, i.e., the photosensor $P_{X1}$, the photosensor $P_{X2}$, the photosensor $P_{X3}$, and the photosensor $P_{X4}$. The four photosensors $P_{X1}$, $P_{X2}$, $P_{X3}$, and $P_{X4}$ may be arranged parallel to the Y axis direction. More descriptions of the arrangement of the photosensors $P_{Y1}$, $P_{Y2}$, $P_{Y3}$, $P_{Y4}$, $P_{X1}$, $P_{X2}$, $P_{X3}$, and $P_{X4}$ may be found elsewhere in the present disclosure. See, for example, FIGS. 4A-4D and the description thereof.

Figure 3B:
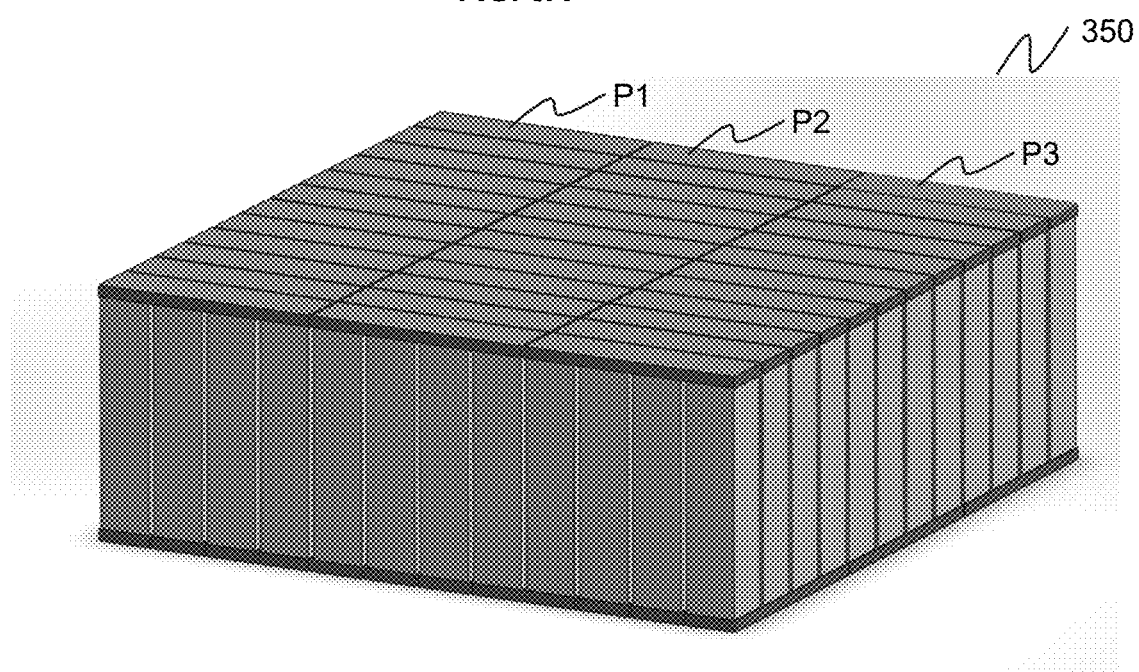
FIG. 3B is a schematic diagram illustrating an exemplary detector according to some embodiments of the present disclosure.

FIG. 3B is a schematic diagram illustrating an exemplary detector 350 according to some embodiments of the present disclosure. The detector 350 may include one or more detector modules 300. For example, the detector 350 may include 3×3 detector modules 300. Further, one or more detectors 350 may be assembled to form the detector assembly 112. As illustrated in FIG. 3B, the detector 350 may include a 12×12 scintillator array, a 12×3 photosensor array 220a, and a 3×12 photosensor array 220b. In some embodiments, at least two of the photosensors in the same row (e.g., the photosensor P1, the photosensor P2, and the photosensor P3) may be integrated into one photosensor.

It should be noted that the numbers mentioned in FIGS. 3A and 3B, and the arrangement of the photosensors are merely provided for the purpose of illustration, and not intended to limit the scope of the present disclosure. For example, the detector module 300 may include 5×5 scintillators, 6×6 scintillators, 3×4 scintillators, etc. As another example, the detector 350 may include 4×4 detector modules 300, 5×5 detector modules 300, 6×8 detector modules 300, etc.

Figure 4A:
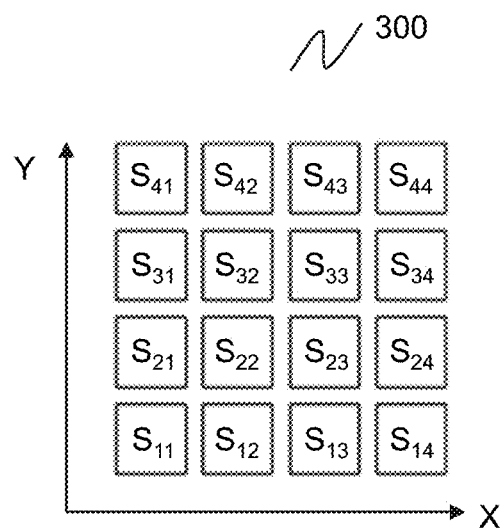
FIG. 4A is a schematic diagram illustrating a top view of a 4×4 scintillator array of an exemplary detector module according to some embodiments of the present disclosure.

FIG. 4A is a schematic diagram illustrating a top view of a 4×4 scintillator array 210 of an exemplary detector module 300 according to some embodiments of the present disclosure. A 3D stereogram of the detector module 300 may be found in FIG. 3A. As illustrated in FIG. 4A, the 4×4 scintillator array 210 may include 4 rows of scintillators including, a first row of scintillators $S_{11}$, $S_{12}$, $S_{13}$, and $S_{14}$, a second row of scintillators $S_{21}$, $S_{22}$, $S_{23}$, and $S_{24}$, a third row of scintillators $S_{31}$, $S_{32}$, $S_{33}$, and $S_{34}$, and a fourth row of scintillators $S_{41}$, $S_{42}$, $S_{43}$, and $S_{44}$. The first row of scintillators $S_{11}$, $S_{12}$, $S_{13}$, and $S_{14}$ may be arranged along the X axis direction. The second row of scintillators $S_{21}$, $S_{22}$, $S_{23}$, and $S_{24}$ may be arranged along the X axis direction. The third row of scintillators $S_{31}$, $S_{32}$, $S_{33}$, and $S_{34}$ may be arranged along the X axis direction. The fourth row of scintillators $S_{41}$, $S_{42}$, $S_{43}$, and $S_{44}$ may be arranged along the X axis direction. As illustrated, the 4×4 scintillator array 210 may include 4 columns of scintillators including, a first column of scintillators $S_{11}$, $S_{21}$, $S_{31}$, and $S_{41}$, a second column of scintillators $S_{12}$, $S_{22}$, $S_{32}$, and $S_{42}$, a third column of scintillators $S_{13}$, $S_{23}$, $S_{33}$, and $S_{43}$, and a fourth column of scintillators $S_{14}$, $S_{24}$, $S_{34}$, and $S_{44}$. The first column of scintillators $S_{11}$, $S_{21}$, $S_{31}$, and $S_{41}$ may be arranged along the Y axis direction. The second column of scintillators $S_{12}$, $S_{22}$, $S_{32}$, and $S_{42}$ may be arranged along the Y axis direction. The third column of scintillators $S_{13}$, $S_{23}$, $S_{33}$, and $S_{43}$ may be arranged along the Y axis direction. The fourth column of scintillators $S_{14}$, $S_{24}$, $S_{34}$, and $S_{44}$ may be arranged along the Y axis direction.

In some embodiments, two adjacent scintillators may be separated by a certain distance. The distance between two adjacent scintillators may be small relative to the dimension of a scintillator in the same direction of the distance and/or the dimension of a photosensor in the same direction of the distance. For example, the distance between two adjacent scintillators may be a fraction (e.g., 1/10, 1/20, 1/30, etc.) of the dimension of a scintillator and/or the dimension of a photosensor in the same direction of the distance. In some embodiments, the spacing between two adjacent scintillators may be filled with a blocking material (e.g., a light-reflective material in the form of, e.g., films, blocks, etc.). In some embodiments, the spacing between two adjacent scintillators may be void (e.g., vacuum or filled with air, or another gas).

Figure 4B:
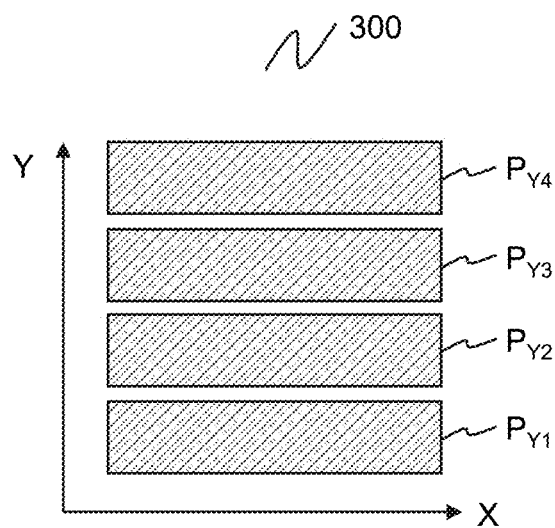
FIG. 4B is a schematic diagram illustrating a top view of a 4×1 first photosensor array of an exemplary detector module according to some embodiments of the present disclosure.

FIG. 4B is a schematic diagram illustrating a top view of a 4×1 first photosensor array 220a of an exemplary detector module 300 according to some embodiments of the present disclosure. The 4×1 first photosensor array 220a may be arranged on a top surface of the 4×4 scintillator array 210 shown in FIGS. 3A, 3B, and 4A. As illustrated in FIG. 4B, the 4×1 first photosensor array 220a may include four rows of photosensors including, the first row of photosensor $P_{Y1}$, the second row of photosensor $P_{Y2}$, the third row of photosensor $P_{Y3}$, and the fourth row of photosensor $P_{Y4}$. The photosensor $P_{Y1}$ may be arranged parallel to the X axis direction. The photosensor $P_{Y2}$ may be arranged parallel to the X axis direction. The photosensor $P_{Y3}$ may be arranged parallel to the X axis direction. The photosensor $P_{Y4}$ may be arranged parallel to the X axis direction. The four photosensors $P_{Y1}$, $P_{Y2}$, $P_{Y3}$, and $P_{Y4}$ may be arranged along the Y axis direction to form a column of photosensors. The photosensor $P_{Y1}$ may be optically coupled to the first row of scintillators $S_{11}$, $S_{12}$, $S_{13}$ and $S_{14}$ shown in FIG. 4A. The photosensor $P_{Y2}$ may be optically coupled to the second row of scintillators $S_{21}$, $S_{22}$, $S_{23}$ and $S_{24}$ shown in FIG. 4A. The photosensor $P_{Y3}$ may be optically coupled to the third row of scintillators $S_{31}$, $S_{32}$, $S_{33}$ and $S_{34}$ shown in FIG. 4A. The photosensor $P_{Y4}$ may be optically coupled to the fourth row of scintillators $S_{41}$, $S_{42}$, $S_{43}$ and $S_{44}$ shown in FIG. 4A.

In some embodiments, a first length of a photosensor (e.g., the photosensor $P_{Y1}$, $P_{Y2}$, $P_{Y3}$, or $P_{Y4}$) along the X axis direction may be equal to or different from (e.g., less or larger than) a first sum of the lengths of a row of scintillators along the X axis direction and the spacing there between (if any) along the X axis direction. For example, the difference between the first length and the first sum may be less than the length of two scintillators along the X axis direction. In some embodiments, a first width of a photosensor (e.g., the photosensor $P_{Y1}$, $P_{Y2}$, $P_{Y3}$, or $P_{Y4}$) along the Y axis direction may be equal to or different from (e.g., less or larger than) a second width of one scintillator along the Y axis direction. For example, the first width may be a fraction (e.g., 3/4, 2/3, 1/2, etc.) of the second width. As another example, the first width of a photosensor (e.g., the photosensor $P_{Y1}$, $P_{Y2}$, $P_{Y3}$, or $P_{Y4}$) along the Y axis direction may be slightly larger than the second width of one scintillator along the Y axis direction, and the photosensor is free of contact along the Y axis direction with or otherwise electrically insulated from a neighboring photosensor.

In some embodiments, a 1×4 second photosensor array 220b (see FIG. 3A) may be arranged on a bottom surface of the 4×4 scintillator array 210 shown in FIGS. 3A, 3B, and 4A. The 1×4 second photosensor array 220b may include four columns of photosensors including, the first column of photosensor $P_{X1}$, the second column of photosensor $P_{X2}$, the third column of photosensor $P_{X3}$, and the fourth column of photosensor $P_{X4}$. The photosensor $P_{X1}$ may be arranged parallel to the Y axis direction. The photosensor $P_{X2}$ may be arranged parallel to the Y axis direction. The photosensor $P_{X3}$ may be arranged parallel to the Y axis direction. The photosensor $P_{X4}$ may be arranged parallel to the Y axis direction. The four photosensors $P_{X1}$, $P_{X2}$, $P_{X3}$, and $P_{X4}$ may be arranged along the X axis direction to form a row of photosensor. The photosensor $P_{X1}$ may be optically coupled to the first column of scintillators $S_{11}$, $S_{21}$, $S_{31}$ and $S_{41}$ shown in FIG. 4A. The photosensor $P_{X2}$ may be optically coupled to the second column of scintillators $S_{12}$, $S_{22}$, $S_{32}$ and $S_{42}$ shown in FIG. 4A. The photosensor $P_{X3}$ may be optically coupled to the third column of scintillators $S_{13}$, $S_{23}$, $S_{33}$ and $S_{43}$ shown in FIG. 4A. The photosensor $P_{X4}$ may be optically coupled to the fourth column of scintillators $S_{14}$, $S_{24}$, $S_{34}$ and $S_{44}$ shown in FIG. 4A.

In some embodiments, a second length of a photosensor (e.g., the photosensor $P_{X1}$, $P_{X2}$, $P_{X3}$, or $P_{X4}$) along the Y axis direction may be equal to or different from (e.g., less or larger than) a second sum of the lengths of a column of scintillators along the Y axis direction and the spacing there between (if any) along the Y axis direction. For example, the difference between the second length and the second sum may be less than the length of two scintillators along the Y axis direction. In some embodiments, a third width of a photosensor (e.g., the photosensor $P_{X1}$, $P_{X2}$, $P_{X3}$, or $P_{X4}$) along the X axis direction may be equal to or different from (e.g., less or larger than) a fourth width of one scintillator along the X axis direction. For example, the third width may be a fraction (e.g., 3/4, 2/3, 1/2, etc.) of the fourth width. As another example, the third width of a photosensor (e.g., the photosensor $P_{X1}$, $P_{X2}$, $P_{X3}$, or $P_{X4}$) along the X axis direction may be slightly larger than the fourth width of one scintillator along the X axis direction, and the photosensor is free of contact along the X axis direction with or otherwise electrically insulated from a neighboring photosensor.

Figure 4C:
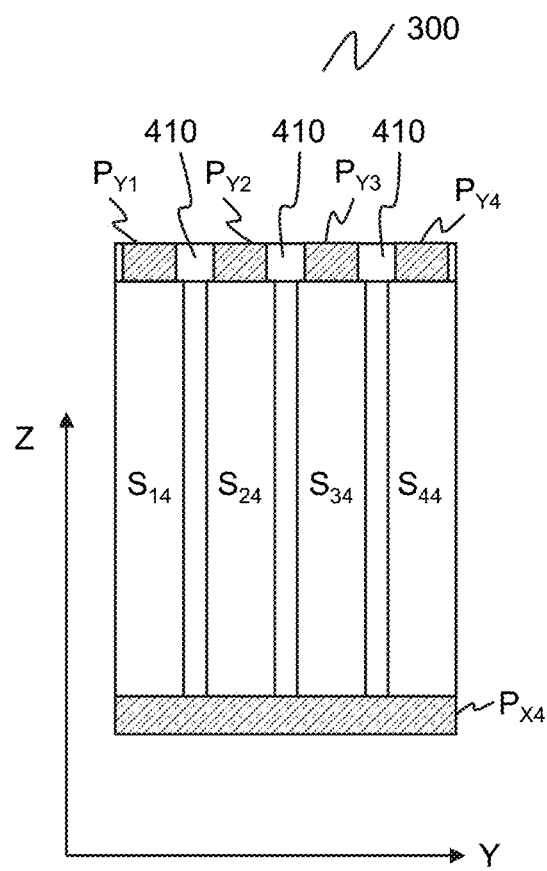
FIG. 4C is a schematic diagram illustrating a right view of an exemplary detector module according to some embodiments of the present disclosure.

FIG. 4C is a schematic diagram illustrating a right view of an exemplary detector module 300 according to some embodiments of the present disclosure. As illustrated in FIG. 4C, the photosensor $P_{X4}$ may be optically coupled to the scintillators $S_{14}$, $S_{24}$, $S_{34}$ and $S_{44}$. A portion of the photosensor $P_{Y1}$ may be optically coupled to the scintillator $S_{14}$. A portion of the photosensor $P_{Y2}$ may be optically coupled to the scintillator $S_{24}$. A portion of the photosensor $P_{Y3}$ may be optically coupled to the scintillator $S_{34}$. A portion of the photosensor $P_{Y4}$ may be optically coupled to the scintillator $S_{44}$. As mentioned above, the length of the photosensor $P_{X4}$ along the Y axis direction may be equal to or less than a sum of the lengths of a column of scintillators $S_{14}$, $S_{24}$, $S_{34}$, and $S_{44}$ along the Y axis direction and the spacing there between (if any) along the Y axis direction. As mentioned above, the width of the photosensor $P_{Y1}$, $P_{Y2}$, $P_{Y3}$, or $P_{Y4}$ along the Y axis direction may be equal to or less than the width of the scintillator $S_{14}$, $S_{24}$, $S_{34}$, or $S_{44}$ along the Y axis direction.

Figure 4D:
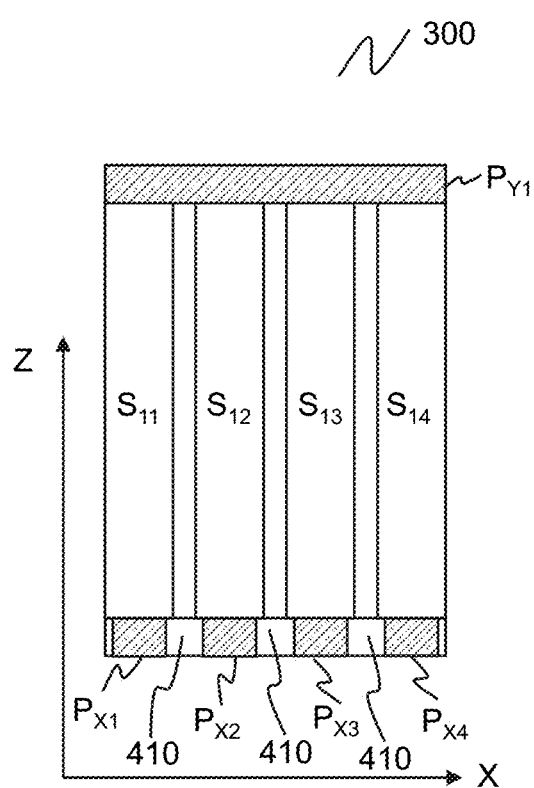
FIG. 4D is a schematic diagram illustrating a front view of an exemplary detector module according to some embodiments of the present disclosure.

FIG. 4D is a schematic diagram illustrating a front view of an exemplary detector module 300 according to some embodiments of the present disclosure. As illustrated in FIG. 4D, the photosensor $P_{Y1}$ may be optically coupled to the scintillators $S_{11}$, $S_{12}$, $S_{13}$, and $S_{14}$. A portion of the photosensor $P_{X1}$ may be optically coupled to the scintillator $S_{11}$. A portion of the photosensor $P_{X2}$ may be optically coupled to the scintillator $S_{12}$. A portion of the photosensor $P_{X3}$ may be optically coupled to the scintillator $S_{13}$. A portion of the photosensor $P_{X4}$ may be optically coupled to the scintillator $S_{14}$. As mentioned above, the length of the photosensor $P_{Y1}$ along the X axis direction may be equal to or less than a sum of the lengths of a row of scintillators $S_{11}$, $S_{12}$, $S_{13}$, and $S_{14}$ along the X axis direction and the spacing there between (if any) along the X axis direction. As mentioned above, the width of the photosensor $P_{X1}$, $P_{X2}$, $P_{X3}$, or $P_{X4}$ along the X axis direction may be equal to or less than the width of the scintillator $S_{11}$, $S_{12}$, $S_{13}$, or $S_{14}$ along the X axis direction.

As illustrated in FIGS. 4C and 4D, two adjacent photosensors may be separated by a certain distance. The distance between two adjacent photosensors may be determined based on the size and/or arrangement of the photosensors. For example, the distance between two adjacent photosensors (e.g., $P_{Y1}$, $P_{Y2}$, $P_{Y3}$, and/or $P_{Y4}$) may be less than the width of the scintillator $S_{14}$, $S_{24}$, $S_{34}$ or $S_{44}$ along the Y axis direction. In some embodiments, the spacing 410 between two adjacent photosensors may be filled with an isolation material (e.g., an electrical insulating material, polymers, etc.). In some embodiments, the spacing 410 between two adjacent photosensors may be void (e.g., vacuum or filled with air, or another gas).

FIG. 5A is a schematic diagram illustrating a top view of a 4×4 scintillator array 210 of an exemplary detector module 500 according to some embodiments of the present disclosure. More descriptions of the 4×4 scintillator array 210 may be found elsewhere in the present disclosure. See, for example, FIG. 4A and the description thereof.

FIG. 5B is a schematic diagram illustrating a top view of a 4×4 first photosensor array 220a of an exemplary detector module 500 according to some embodiments of the present disclosure. The 4×4 first photosensor array 220a may be arranged on the top surface of the 4×4 scintillator array 210 shown in FIG. 5A. The arrangement of the 4×4 first photosensor array 220a in the X-Y plane may be similar with the 4×4 scintillator array 210 as illustrated in FIG. 5A. The photosensors $P_{11}$, $P_{12}$, $P_{13}$, $P_{14}$, $P_{21}$, $P_{22}$, $P_{23}$, $P_{24}$, $P_{31}$, $P_{32}$, $P_{33}$, $P_{34}$, $P_{41}$, $P_{42}$, $P_{43}$, and $P_{44}$ may be optically coupled to the scintillators $S_{11}$, $S_{12}$, $S_{13}$, $S_{14}$, $S_{21}$, $S_{22}$, $S_{23}$, $S_{24}$, $S_{31}$, $S_{32}$, $S_{33}$, $S_{34}$, $S_{41}$, $S_{42}$, $S_{43}$, and $S_{44}$ respectively.

In some embodiments, a 4×4 second photosensor array 220b may be optically coupled to the 4×4 scintillator array 210 shown in FIG. 5A. The 4×4 second photosensor array 220b may include 16 photosensors $P'_{11}$, $P'_{12}$, $P'_{13}$, $P'_{14}$, $P'_{21}$, $P'_{22}$, $P'_{23}$, $P'_{24}$, $P'_{31}$, $P'_{32}$, $P'_{33}$, $P'_{34}$, $P'_{41}$, $P'_{42}$, $P'_{43}$, and $P'_{44}$. The 4×4 second photosensor array 220b may be arranged on the bottom surface of the 4×4 scintillator array 210 shown in FIG. 5A. The arrangement of the 4×4 second photosensor array 220b in the X-Y plane may be similar to the 4×4 scintillator array 210 as illustrated in FIG. 5A. The photosensors $P'_{11}$, $P'_{12}$, $P'_{13}$, $P'_{14}$, $P'_{21}$, $P'_{22}$, $P'_{23}$, $P'_{24}$, $P'_{31}$, $P'_{32}$, $P'_{33}$, $P'_{34}$, $P'_{41}$, $P'_{42}$, $P'_{43}$, and $P'_{44}$ may be optically coupled to the scintillators $S_{11}$, $S_{12}$, $S_{13}$, $S_{14}$, $S_{21}$, $S_{22}$, $S_{23}$, $S_{24}$, $S_{31}$, $S_{32}$, $S_{33}$, $S_{34}$, $S_{41}$, $S_{42}$, $S_{43}$, and $S_{44}$, respectively.

FIG. 5C is a schematic diagram illustrating a right view of an exemplary detector module 500 according to some embodiments of the present disclosure. FIG. 5D is a schematic diagram illustrating a front view of an exemplary detector module 500 according to some embodiments of the present disclosure. The spacing 510 between two adjacent photosensors may be similar to the spacing 410 illustrated in FIGS. 4C and 4D.

It should be noted that the numbers mentioned in FIGS. 5A-5D, and the arrangement of the photosensors and the scintillators are merely provided for the purpose of illustration, and not intended to limit the scope of the present disclosure. For persons having ordinary skills in the art, multiple variations and modifications may be made to the detector module 500 under the teachings of the present disclosure. However, those variations and modifications do not depart from the scope of the present disclosure. For example, the 4×4 first photosensor array 220a or the 4×4 second photosensor array 220b may be unnecessary. As another example, the 4×4 first photosensor array 220a or the 4×4 second photosensor array 220b may be replaced by a 4×1 photosensor array 220 or a 1×4 photosensor array 220 as illustrated in FIGS. 4B-4D.

Figure 6A:
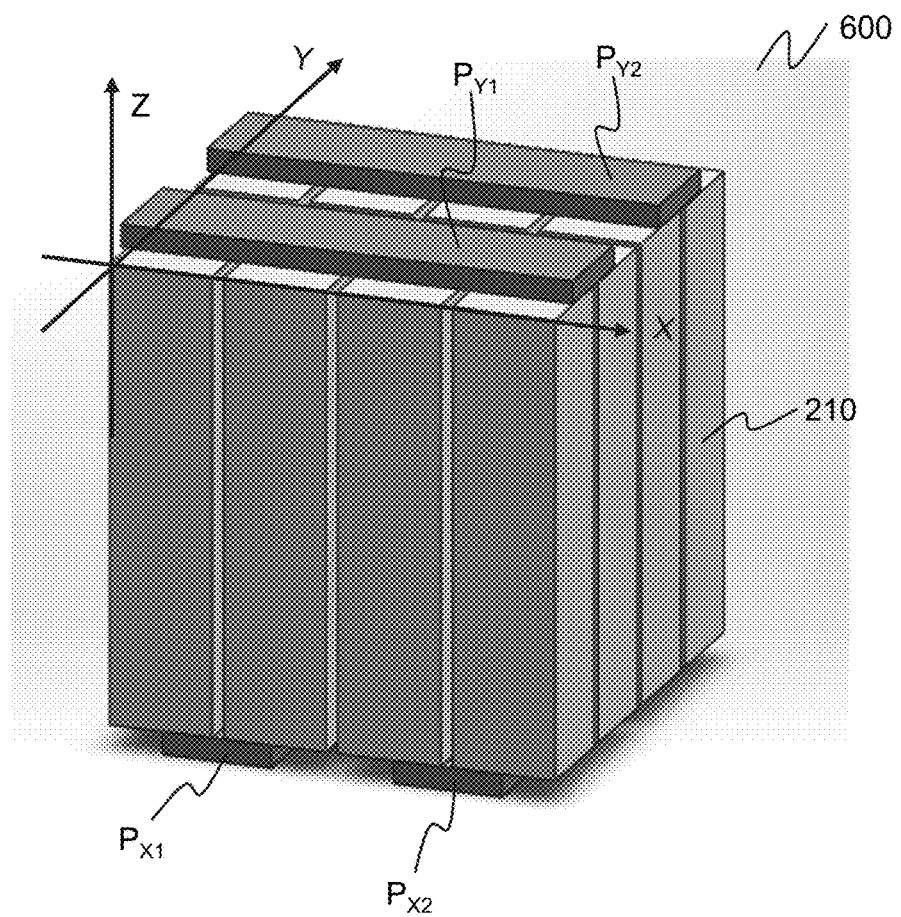
FIG. 6A is a schematic diagram illustrating an exemplary detector module according to some embodiments of the present disclosure.

FIG. 6A is a schematic diagram illustrating an exemplary detector module 600 according to some embodiments of the present disclosure. The detector module 600 may include a 4×4 scintillator array 210, two photosensors (e.g., SiPM) within the first photosensor array 220a, and two photosensors (e.g., SiPM) within the second photosensor array 220b. More descriptions of the 4×4 scintillator array 210 may be found elsewhere in the present disclosure. See, for example, FIG. 3A and the description thereof.

The first photosensor array 220a may be optically coupled to the 4×4 scintillator array 210 and arranged on the top surface. The first photosensor array 220a may include two photosensors, i.e., the photosensor $P_{Y1}$ and the photosensor $P_{Y2}$. The two photosensors $P_{Y1}$ and $P_{Y2}$ may both be arranged parallel to the X axis direction. The second photosensor array 220b may be optically coupled to the 4×4 scintillator array 210 and arranged on the bottom surface. The second photosensor array 220b may include two photosensors, i.e., the photosensor $P_{X1}$ and the photosensor $P_{X2}$. The two photosensors $P_{X1}$ and $P_{X2}$ may both be arranged parallel to the Y axis direction. More descriptions of the arrangement of the photosensors $P_{Y1}$, $P_{Y2}$, $P_{X1}$, and $P_{X2}$ may be found elsewhere in the present disclosure. See, for example, FIGS. 7A-7D and the description thereof.

Figure 6B:
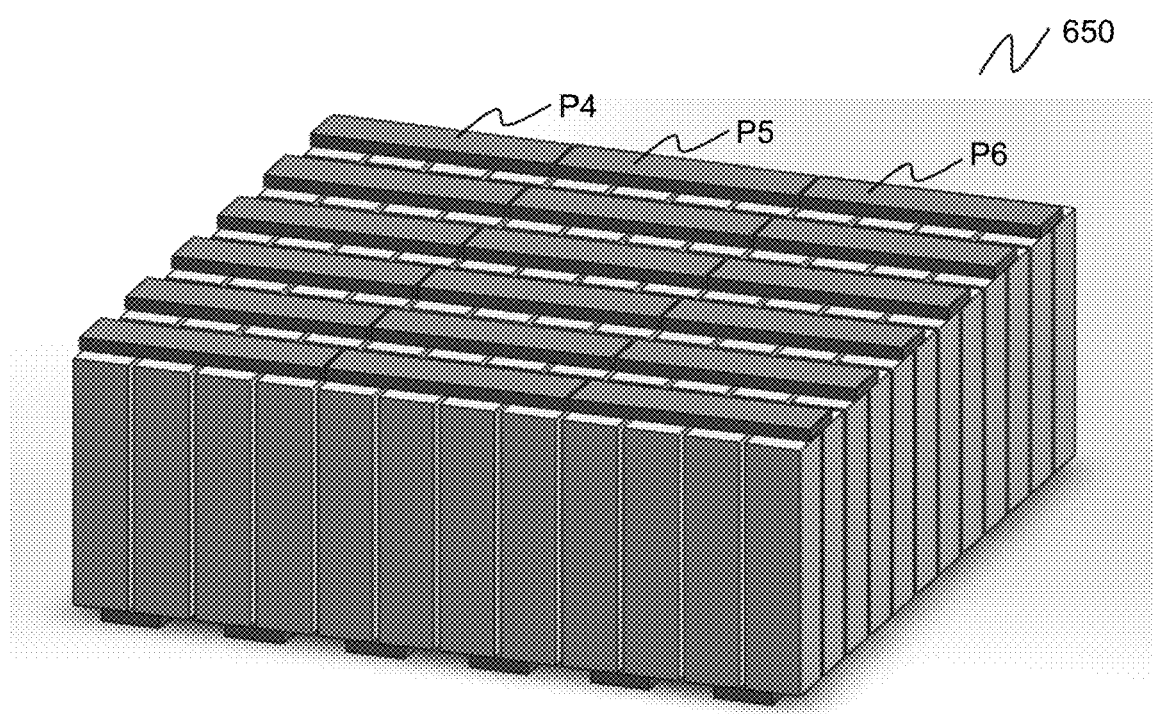
FIG. 6B is a schematic diagram illustrating an exemplary detector according to some embodiments of the present disclosure.

FIG. 6B is a schematic diagram illustrating an exemplary detector 650 according to some embodiments of the present disclosure. The detector 650 may include one or more detector modules 600. For example, the detector 650 may include 3×3 detector modules 600. Further, one or more detectors 650 may be assembled to form the detector assembly 112. As illustrated in FIG. 6B, the detector 650 may include a 12×12 scintillator array, a 6×3 photosensor array 220a, a 3×6 photosensor array 220b. In some embodiments, the photosensors in the same row (e.g., the photosensor P4, the photosensor P5, and the photosensor P6) may be integrated into one photosensor.

It should be noted that the numbers mentioned in FIGS. 6A and 6B, and the arrangement of the photosensors are merely provided for the purpose of illustration, and not intended to limit the scope of the present disclosure. For example, the detector module 600 may include 5×5 scintillators, 6×6 scintillators, 3×4 scintillators, etc. As another example, the detector 650 may include 4×4 detector modules 600, 5×5 detector modules 600, 6×8 detector modules 600, etc.

FIG. 7A is a schematic diagram illustrating a top view of a 4×4 scintillator array 210 of an exemplary detector module 600 according to some embodiments of the present disclosure. A 3D stereogram of the detector module 600 may be shown in FIG. 6A. More descriptions of the 4×4 scintillator array 210 may be found elsewhere in the present disclosure. See, for example, FIG. 4A and the description thereof.

FIG. 7B is a schematic diagram illustrating a top view of a 2×1 first photosensor array 220a of an exemplary detector module 600 according to some embodiments of the present disclosure. The 2×1 first photosensor array 220a may be arranged on a top surface of the 4×4 scintillator array 210 shown in FIGS. 6A, 6B, and 7A. As illustrated in FIG. 7B, the 2×1 first photosensor array 220a may include two rows of photosensors including, the first row of photosensor $P_{Y1}$ and the second row of photosensor $P_{Y2}$. The photosensor $P_{Y1}$ may be arranged parallel to the X axis direction. The photosensor $P_{Y2}$ may be arranged parallel to the X axis direction. The two photosensors $P_{Y1}$ and $P_{Y2}$ may be arranged along the Y axis direction to form a column of photosensors. The photosensor $P_{Y1}$ may be optically coupled to the first row of scintillators $S_{11}$, $S_{12}$, $S_{13}$, $S_{14}$, and the second row of scintillators $S_{21}$, $S_{22}$, $S_{23}$, $S_{24}$ shown in FIG. 7A. The photosensor $P_{Y2}$ may be optically coupled to the third row of scintillators $S_{31}$, $S_{32}$, $S_{33}$, $S_{34}$ and the fourth row of scintillators $S_{41}$, $S_{42}$, $S_{43}$, $S_{44}$ shown in FIG. 7A.

In some embodiments, a first length of a photosensor (e.g., the photosensor $P_{Y1}$ or $P_{Y2}$) along the X axis direction may be equal to or different from (e.g., less or larger than) a first sum of the lengths of a row of scintillators along the X axis direction and the spacing there between (if any) along the X axis direction. For example, the difference between the first length and the first sum may be less than the length of two scintillators along the X axis direction. In some embodiments, a first width of a photosensor (e.g., the photosensor $P_{Y1}$ or $P_{Y2}$) along the Y axis direction may be equal to or different from (e.g., less or larger than) a second width of one scintillator along the Y axis direction. For example, the first width may be a fraction (e.g., ¾, ⅔, ½, etc.) of the second width. Therefore, at least one portion of a scintillator may not be covered by a photosensor. In some embodiments, the area of the photosensor $P_{Y1}$ may be a fraction (e.g., ¾, ⅔, ½, etc.) of a sum of areas of the scintillators to which the photosensor $P_{Y1}$ is optically coupled (i.e., scintillators $S_{11}$, $S_{12}$, $S_{13}$, $S_{14}$, $S_{21}$, $S_{22}$, $S_{23}$, and $S_{24}$). In some embodiments, the area of the photosensor $P_{Y2}$ may be a fraction (e.g., ¾, ⅔, ½, etc.) of a sum of areas of the scintillators to which the photosensor $P_{Y2}$ is optically coupled (i.e., scintillators $S_{31}$, $S_{32}$, $S_{33}$, $S_{34}$, $S_{41}$, $S_{42}$, $S_{43}$, and $S_{44}$). As another example, the first width of a photosensor (e.g., the photosensor $P_{Y1}$ or $P_{Y2}$) along the Y axis direction may be slightly larger than the second width of one scintillator along the Y axis direction, and the photosensor is free of contact along the Y axis direction with or otherwise electrically insulated from a neighboring photosensor.

In some embodiments, a 1×2 second photosensor array 220b (see FIG. 6A) may be arranged on a bottom surface of the 4×4 scintillator array 210 shown in FIGS. 6A, 6B, and 7A. The 1×2 second photosensor array 220b may include two columns of photosensors including, the first column of photosensor $P_{X1}$ and the second column of photosensor $P_{X2}$. The photosensor $P_{X1}$ may be arranged parallel to the Y axis direction. The photosensor $P_{X2}$ may be arranged parallel to the Y axis direction. The two photosensors $P_{X1}$ and $P_{X2}$ may be arranged along the X axis direction to form a row of photosensors. The photosensor $P_{X1}$ may be optically coupled to the first column of scintillators $S_{11}$, $S_{21}$, $S_{31}$, $S_{41}$ and the second column of scintillators $S_{12}$, $S_{22}$, $S_{32}$, $S_{42}$ shown in FIG. 7A. The photosensor $P_{X2}$ may be optically coupled to the third column of scintillators $S_{13}$, $S_{23}$, $S_{33}$, $S_{43}$ and the fourth column of scintillators $S_{14}$, $S_{24}$, $S_{34}$, $S_{44}$ shown in FIG. 7A.

In some embodiments, a second length of a photosensor (e.g., the photosensor $P_{X1}$ or $P_{X2}$) along the Y axis direction may be equal to or different from (e.g., less or larger than) a second sum of the lengths of a column of scintillators along the Y axis direction and the spacing there between (if any) along the Y axis direction. For example, the difference between the second length and the second sum may be less than the length of two scintillators along the Y axis direction. In some embodiments, a third width of a photosensor (e.g., the photosensor $P_{X1}$ or $P_{X2}$) along the X axis direction may be equal to or different from (e.g., less or larger than) a fourth width of one scintillator along the X axis direction. For example, the third width may be a fraction (e.g., ¾, ⅔, ½, etc.) of the fourth width. As another example, the third width of a photosensor (e.g., the photosensor $P_{X1}$ or $P_{X2}$) along the X axis direction may be slightly larger than the fourth width of one scintillator along the X axis direction, and the photosensor is free of contact along the X axis direction with or otherwise electrically insulated from a neighboring photosensor.

FIG. 7C is a schematic diagram illustrating a right view of an exemplary detector module 600 according to some embodiments of the present disclosure. As illustrated in FIG. 7C, a portion of the photosensor $P_{X2}$ may be optically coupled to the scintillators $S_{14}$, $S_{24}$, $S_{34}$ and $S_{44}$. A portion of the photosensor $P_{Y1}$ may be optically coupled to the scintillators $S_{14}$ and $S_{24}$. A portion of the photosensor $P_{Y2}$ may be optically coupled to the scintillators $S_{34}$ and $S_{44}$. As mentioned above, the length of the photosensor $P_{X2}$ along the Y axis direction may be equal to or less than a sum of the lengths of a column of scintillators $S_{14}$, $S_{24}$, $S_{34}$ and $S_{44}$ along the Y axis direction and the spacing there between (if any) along the Y axis direction. As mentioned above, the width of the photosensor $P_{Y1}$ (or $P_{Y2}$) along the Y axis direction may be equal to or less than the width of the scintillator $S_{14}$, $S_{24}$, $S_{34}$, or $S_{44}$ along the Y axis direction.

FIG. 7D is a schematic diagram illustrating a front view of an exemplary detector module 600 according to some embodiments of the present disclosure. As illustrated in FIG. 7D, a portion of the photosensor $P_{Y1}$ may be optically coupled to the scintillators $S_{11}$, $S_{12}$, $S_{13}$ and $S_{14}$. A portion of the photosensor $P_{X1}$ may be optically coupled to the scintillators $S_{11}$ and $S_{12}$. A portion of the photosensor $P_{X2}$ may be optically coupled to the scintillators $S_{13}$ and $S_{14}$. As mentioned above, the length of the photosensor $P_{Y1}$ along the X axis direction may be equal to or less than a sum of the lengths of a row of scintillators $S_{11}$, $S_{12}$, $S_{13}$ and $S_{14}$ along the X axis direction and the spacing there between (if any) along the X axis direction. As mentioned above, the width of the photosensor $P_{X1}$ or $P_{X2}$ along the X axis direction may be equal to or less than the width of the scintillator $S_{11}$, $S_{12}$, $S_{13}$ or $S_{14}$ along the X axis direction.

As illustrated in FIGS. 7C and 7D, two adjacent photosensors may be separated by a certain distance. The distance between two adjacent photosensors may be determined based on the size and/or arrangement of the photosensors. For example, the distance between two adjacent photosensors $P_{Y1}$ and $P_{Y2}$ may be larger than the width of the scintillator $S_{14}$, $S_{24}$, $S_{34}$ or $S_{44}$ along the Y axis direction. In some embodiments, the spacing 710 between two adjacent photosensors may be filled with an isolation material (e.g., an electrical insulating material, polymers, etc.). In some embodiments, the spacing 710 between two adjacent photosensors may be void (e.g., vacuum or filled with air, or another gas).

Figure 8A:
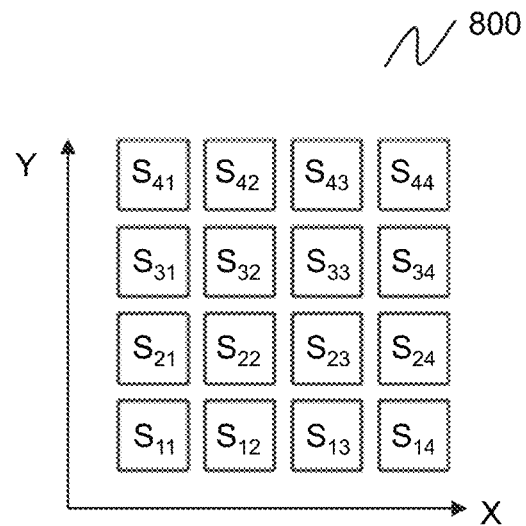
FIG. 8A is a schematic diagram illustrating a top view of a 4×4 scintillator array of an exemplary detector module according to some embodiments of the present disclosure.

FIG. 8A is a schematic diagram illustrating a top view of a 4×4 scintillator array 210 of an exemplary detector module 800 according to some embodiments of the present disclosure. More descriptions of the 4×4 scintillator array 210 may be found elsewhere in the present disclosure. See, for example, FIG. 4A and the description thereof.

Figure 8B:
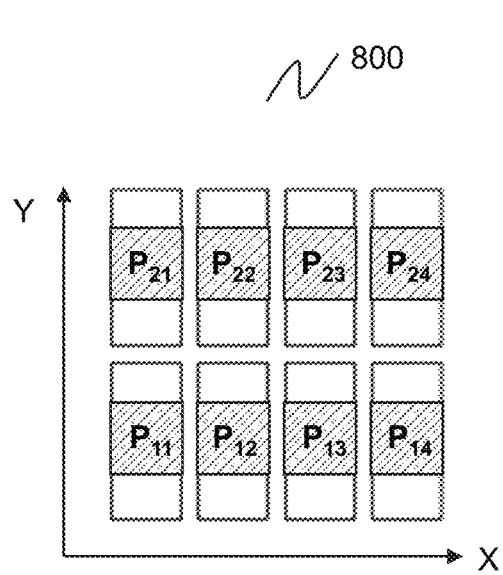
FIG. 8B is a schematic diagram illustrating a top view of a 2×4 first photosensor array of an exemplary detector module according to some embodiments of the present disclosure.

FIG. 8B is a schematic diagram illustrating a top view of a 2×4 first photosensor array 220a of an exemplary detector module 800 according to some embodiments of the present disclosure. The 2×4 first photosensor array 220a may be arranged on a top surface of the 4×4 scintillator array 210 shown in FIG. 8A. As illustrated in FIG. 8B, the 2×4 first photosensor array 220a may include two rows of photosensors including, the first row of photosensors (i.e., $P_{11}$, $P_{12}$, $P_{13}$, $P_{14}$), and the second row of photosensors (i.e., $P_{21}$, $P_{22}$, $P_{23}$, $P_{24}$). The first (or second) row of photosensors may be arranged along the X axis direction. The 2×4 first photosensor array 220a may include four columns of photosensors including, the first column of photosensors (i.e., $P_{11}$, $P_{21}$), the second column of photosensors (i.e., $P_{12}$, $P_{22}$), the third column of photosensors (i.e., $P_{13}$, $P_{23}$), and the fourth column of photosensors (i.e., $P_{14}$, $P_{24}$). The first (second, third, or fourth) column of photosensors may be arranged along the Y axis direction.

The photosensor $P_{11}$ may be optically coupled to the scintillators $S_{11}$ and $S_{21}$ shown in FIG. 7A. The photosensor $P_{12}$ may be optically coupled to the scintillators $S_{12}$ and $S_{22}$ shown in FIG. 7A. The photosensor $P_{13}$ may be optically coupled to the scintillators $S_{13}$ and $S_{23}$ shown in FIG. 7A. The photosensor $P_{14}$ may be optically coupled to the scintillators $S_{14}$ and $S_{24}$ shown in FIG. 7A. The photosensor $P_{21}$ may be optically coupled to the scintillators $S_{31}$ and $S_{41}$ shown in FIG. 7A. The photosensor $P_{22}$ may be optically coupled to the scintillators $S_{32}$ and $S_{42}$ shown in FIG. 7A. The photosensor $P_{23}$ may be optically coupled to the scintillators $S_{33}$ and $S_{43}$ shown in FIG. 7A. The photosensor $P_{24}$ may be optically coupled to the scintillators $S_{34}$ and $S_{44}$ shown in FIG. 7A.

In some embodiments, a length of a photosensor (e.g., the photosensor $P_{11}$, $P_{12}$, $P_{13}$, $P_{14}$, $P_{21}$, $P_{22}$, $P_{23}$, or $P_{24}$) along the X axis direction may be equal to or different from (e.g., less or larger than) the width of a scintillator within the 4×4 scintillator array 210. In some embodiments, a width of a photosensor (e.g., the photosensor $P_{11}$, $P_{12}$, $P_{13}$, $P_{14}$, $P_{21}$, $P_{22}$, $P_{23}$, or $P_{24}$) along the Y axis direction may be equal to or different from (e.g., less or larger than) a sum of widths along the Y axis direction of the scintillators to which the photosensor is optically coupled to. For example, the width may be a fraction (e.g., ¾, ⅔, ½, etc.) of the sum. Therefore, at least one portion of a scintillator may not be covered by a photosensor. In some embodiments, the area of a photosensor (e.g., $P_{11}$) may be a fraction (e.g., ¾, ⅔, ½, etc.) of a sum of areas of the scintillators (e.g., $S_{11}$ and $S_{21}$) to which the photosensor is optically coupled. As another example, the width of a photosensor (e.g., the photosensor $P_{11}$, $P_{12}$, $P_{13}$, $P_{14}$, $P_{21}$, $P_{22}$, $P_{23}$, or $P_{24}$) along the Y axis direction may be slightly larger than the sum of widths along the Y axis direction of the scintillators to which the photosensor is optically coupled to, and the photosensor is free of contact along the Y axis direction with or otherwise electrically insulated from a neighboring photosensor.

Figure 8C:
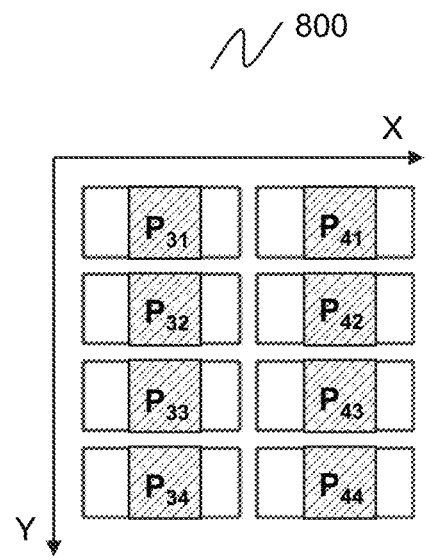
FIG. 8C is a schematic diagram illustrating a bottom view of a 4×2 second photosensor array of an exemplary detector module according to some embodiments of the present disclosure.

FIG. 8C is a schematic diagram illustrating a bottom view of a 4×2 second photosensor array 220b of an exemplary detector module 800 according to some embodiments of the present disclosure. The 4×2 second photosensor array 220b may include four rows of photosensors including, the first row of photosensors (i.e., $P_{31}$, $P_{41}$), the second row of photosensors (i.e., $P_{32}$, $P_{42}$), the third row of photosensors (i.e., $P_{33}$, $P_{43}$), and the fourth row of photosensors (i.e., $P_{34}$, $P_{44}$). The first (second, third, or fourth) row of photosensors may be arranged along the X axis direction. The 4×2 second photosensor array 220b may include two columns of photosensors including, the first column of photosensors (i.e., $P_{31}$, $P_{32}$, $P_{33}$, $P_{34}$), and the second column of photosensors (i.e., $P_{41}$, $P_{42}$, $P_{43}$, $P_{44}$). The first (or second) column of photosensors may be arranged along the Y axis direction.

The photosensor $P_{31}$ may be optically coupled to the scintillators $S_{11}$ and $S_{12}$ shown in FIG. 7A. The photosensor $P_{32}$ may be optically coupled to the scintillators $S_{21}$ and $S_{22}$ shown in FIG. 7A. The photosensor $P_{33}$ may be optically coupled to the scintillators $S_{31}$ and $S_{32}$ shown in FIG. 7A. The photosensor $P_{34}$ may be optically coupled to the scintillators $S_{41}$ and $S_{42}$ shown in FIG. 7A. The photosensor $P_{41}$ may be optically coupled to the scintillators $S_{13}$ and $S_{14}$ shown in FIG. 7A. The photosensor $P_{42}$ may be optically coupled to the scintillators $S_{23}$ and $S_{24}$ shown in FIG. 7A. The photosensor $P_{43}$ may be optically coupled to the scintillators $S_{33}$ and $S_{34}$ shown in FIG. 7A. The photosensor $P_{44}$ may be optically coupled to the scintillators $S_{43}$ and $S_{44}$ shown in FIG. 7A.

In some embodiments, a width of a photosensor (e.g., the photosensor $P_{31}$, $P_{32}$, $P_{33}$, $P_{34}$, $P_{41}$, $P_{42}$, $P_{43}$, or $P_{44}$) along the Y axis direction may be equal to or different from (e.g., less or larger than) the width of a scintillator within the 4×4 scintillator array 210. In some embodiments, a length of a photosensor (e.g., the photosensor $P_{31}$, $P_{32}$, $P_{33}$, $P_{34}$, $P_{41}$, $P_{42}$, $P_{43}$, or $P_{44}$) along the X axis direction may be equal to or different from (e.g., less or larger than) a sum of lengths along the X axis direction of the scintillators to which the photosensor is optically coupled to. For example, the length may be a fraction (e.g., ¾, ⅔, ½, etc.) of the sum. Therefore, at least one portion of a scintillator may not be covered by a photosensor. In some embodiments, the area of a photosensor (e.g., $P_{31}$) may be a fraction (e.g., ¾, ⅔, ½, etc.) of a sum of areas of the scintillators (e.g., $S_{11}$ and $S_{12}$) to which the photosensor is coupled. As another example, the length of a photosensor (e.g., the photosensor $P_{31}$, $P_{32}$, $P_{33}$, $P_{34}$, $P_{41}$, $P_{42}$, $P_{43}$, or $P_{44}$) along the X axis direction may be slightly larger than the sum of lengths along the X axis direction of the scintillators to which the photosensor is optically coupled to, and the photosensor is free of contact along the X axis direction with or otherwise electrically insulated from a neighboring photosensor.

Figures 8D, 8E:
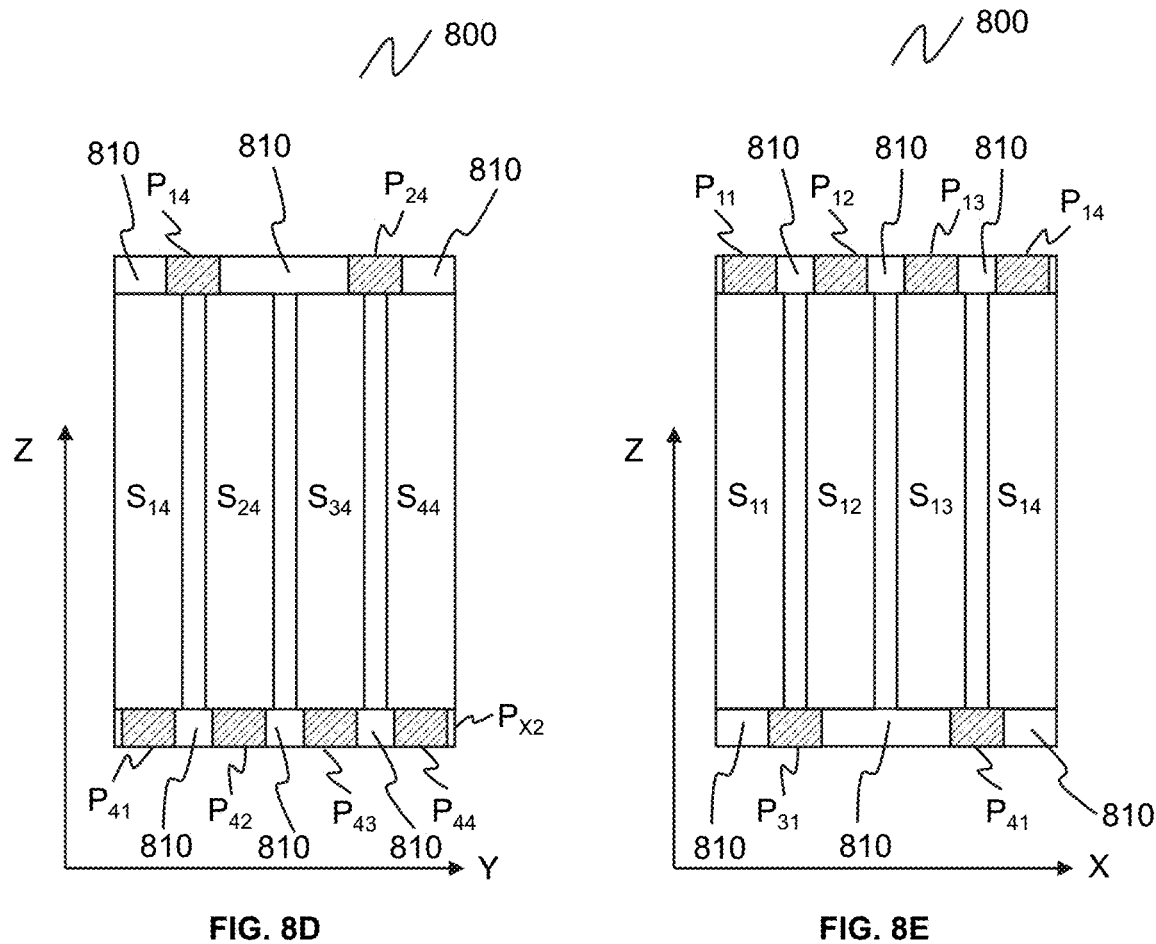
FIG. 8D is a schematic diagram illustrating a right view of an exemplary detector module according to some embodiments of the present disclosure.
FIG. 8E is a schematic diagram illustrating a front view of an exemplary detector module according to some embodiments of the present disclosure.

FIG. 8D is a schematic diagram illustrating a right view of an exemplary detector module 800 according to some embodiments of the present disclosure. As illustrated in FIG. 8D, a portion of the photosensor $P_{41}$ ($P_{42}$, $P_{43}$, or $P_{44}$) may be optically coupled to the scintillator $S_{14}$ ($S_{24}$, $S_{34}$, or $S_{44}$). The photosensor $P_{14}$ (or $P_{24}$) may be optically coupled to the scintillators $S_{14}$ and $S_{24}$ (or, $S_{34}$ and $S_{44}$). FIG. 8E is a schematic diagram illustrating a front view of an exemplary detector module 800 according to some embodiments of the present disclosure. As illustrated in FIG. 8E, a portion of the photosensor $P_{11}$ ($P_{12}$, $P_{13}$, or $P_{14}$) may be optically coupled to the scintillator $S_{11}$ ($S_{12}$, $S_{13}$, or $S_{14}$). The photosensor $P_{31}$ (or $P_{41}$) may be optically coupled to the scintillators Suu and $S_{12}$ (or, $S_{13}$ and $S_{14}$).

As illustrated in FIGS. 8D and 8E, two adjacent photosensors may be separated by a certain distance. The distance between two adjacent photosensors may be determined based on the size and/or arrangement of the photosensors. For example, the distance between two adjacent photosensors $P_{41}$ and $P_{42}$ may be less than the width of the scintillator $S_{14}$, $S_{24}$, $S_{34}$, or $S_{44}$ along the Y axis direction. As another example, the distance between two adjacent photosensors $P_{14}$ and $P_{24}$ may be larger than the width of the scintillator $S_{14}$, $S_{24}$, $S_{34}$, or $S_{44}$ along the Y axis direction. In some embodiments, the spacing 810 between two adjacent photosensors may be filled with an isolation material (e.g., an electrical insulating material, polymers, etc.). In some embodiments, the spacing 810 between two adjacent photosensors may be void (e.g., vacuum or filled with air, or another gas).

Figure 9:
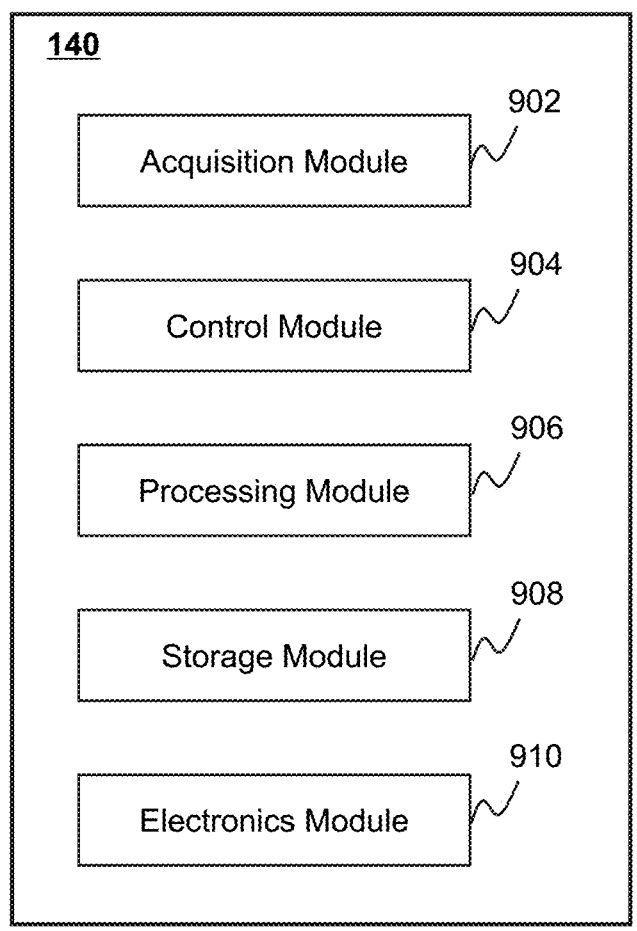
FIG. 9 is a schematic diagram illustrating an exemplary processing engine according to some embodiments of the present disclosure.

FIG. 9 is a schematic diagram illustrating an exemplary processing engine 140 according to some embodiments of the present disclosure. The processing engine 140 may include an acquisition module 902, a control module 904, a processing module 906, a storage module 908, and an electronics module 910.

The acquisition module 902 may acquire data or signal. In some embodiments, the acquisition module 902 may acquire the data from the scanner 110, the storage device 150, the terminal(s) 130, and/or an external data source (not shown). In some embodiments, the data may include image data, instructions, or the like, or a combination thereof. For example, the image data may be generated based on the radiation rays (e.g., γ rays) that emit from a subject positioned in the detection region 113. In some embodiments, the image data may include information relating to energy of the radiation rays (e.g., γ rays), information relating to a hit position of impinging radiation rays (e.g., γ rays) in the scintillator array 210, and/or information relating to a hit time of impinging radiation rays (e.g., γ rays) in the scintillator array 210. The instructions may be executed by the processor(s) of the processing engine 140 to perform exemplary methods described in this disclosure. In some embodiments, the acquired data may be transmitted to the storage module 908 for storing.

Control module 904 may generate one or more control parameters for controlling the acquisition module 902, the processing module 906, the storage module 908, and/or the electronics module 910. For example, the control module 904 may control the acquisition module 902 as to whether to acquire a signal, the time when a signal acquisition may occur, or the frequency to acquire a signal. As another example, the control module 904 may control the processing module 906 to select different algorithms to process the data or signal acquired by the acquisition module 902. In some embodiments, the control module 904 may receive a real-time or a predetermined command provided by a user (e.g., a doctor, a technician, etc.) and adjust the acquisition module 902, and/or the processing module 906 to generate images of a subject according to the received command. In some embodiments, the control module 904 may communicate with other modules in the PET imaging system 100 for exchanging information or data.

The processing module 906 may process information provided by various modules of the processing engine 140. The processing module 906 may process data or signal acquired by the acquisition module 902, data retrieved from the storage module 908, etc. In some embodiments, the processing module 906 may reconstruct one or more images based on the data or signal according to a reconstruction technique, generate reports including the one or more images and/or other related information, and/or perform any other function for image reconstruction. In some embodiments, the processing module 906 may be configured to reconstruct an image based on a first set of electrical signals generated by a first set of photosensors and a second set of electrical signals generated by a second set of photosensors.

The storage module 908 may store data or signal, control parameter(s), processed data or signal, or the like, or a combination thereof. In some embodiments, the storage module 908 may store one or more programs and/or instructions that may be executed by the processor(s) of the processing engine 140 to perform exemplary methods described in this disclosure. For example, the storage module 908 may store program(s) and/or instruction(s) that may be executed by the processor(s) of the processing engine 140 to acquire data or signal, reconstruct an image based on the data or signal, and/or display any intermediate result or a resultant image.

The electronics module 910 may provide electronics support for the implementation of the processing engine 140. In some embodiments, the electronics module 910 may provide electronics support for the acquisition module 902 and/or the processing module 906. The electronics module 910 may collect and/or process the electrical signals generated by the detector assembly 112. The electronics module 910 may include an adder, a multiplier, a subtracter, an amplifier, a drive circuit, a differential circuit, a integral circuit, a counter, a filter, one or more analog-to-digital converters (ADC), a lower limit detection (LLD) circuit, a constant fraction discriminator (CFD) circuit, a time-to-digital converter (TDC), or the like, or any combination thereof. The electronics module 910 may convert an analog signal relating to an energy of radiation rays received by the scintillator array 210 to a digital signal. In some embodiments, the analog-to-digital converter(s) (ADC) may be configured to digitize a first set of electrical signals and a second set of electrical signals. In some embodiments, a time-to-digital converter (TDC) may be configured to determine an interaction time when an impinging radiation ray interacts with an identified scintillator. The electronics module 910 may compare a plurality of digital signals, analyze the plurality of digital signals, and determine a hit position and/or a hit time of the detected radiation rays in the scintillator array 210. In some embodiments, the electronics module 910 may couple to the first set of photosensors (e.g., the first photosensor array 220a) and/or the second set of photosensors (e.g., the second photosensor array 220b). In some embodiments, the electronics module 910 may detect a first set of electrical signals generated by the first set of photosensors and a second set of electrical signals generated by the second set of photosensors. In some embodiments, the electronics module 910 may identify a scintillator within the scintillator array that has interacted with an impinging radiation ray relating to an electrical signal of the first set of electrical signals or the second set of electrical signals. In some embodiments, the electronics module 910 may further determine a depth of interaction of the impinging radiation ray in the identified scintillator. In some embodiments, the electronics module 910 may further include a time correction unit configured to correct the interaction time based on the depth of interaction of an impinging radiation ray. More descriptions of the electronics module 910 may be found elsewhere in the present disclosure. See, for example, FIGS. 12-14 and the description thereof.

In some embodiments, one or more modules illustrated in FIG. 9 may be implemented in at least part of the exemplary PET imaging system 100 as illustrated in FIG. 1. For example, the acquisition module 902, the control module 904, the storage module 908, the processing module 906, and/or the electronics module 910 may be integrated into a console (not shown). Via the console, a user may set the parameters for scanning a subject, acquiring data or signal, view a result in the form of, e.g., an image, text, a table, a curve, etc. In some embodiments, the console may be implemented via the processing engine 140 and/or an external device (not shown).

In some embodiments, the processing engine 140 may be implemented by a computing device. In some embodiments, the processing engine 140, or a portion of the processing engine 140 may be integrated into the scanner 110. In some embodiments, a computing device may include a processor, a storage, an input/output (I/O), and a communication port. The processor may execute computer instructions (e.g., program code) and perform functions of the processing engine 140 in accordance with techniques described herein. The computer instructions may include, for example, routines, programs, objects, components, data structures, procedures, modules, and functions, which perform particular functions described herein. In some embodiments, the processor may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

The storage may store data/information obtained from the scanner 110, the terminal(s) 130, the storage 150, and/or any other component of the imaging system 100. In some embodiments, the storage may include a mass storage, a removable storage, a volatile read-and-write memory, a read-only memory (ROM), or the like, or any combination thereof. For example, the mass storage may include a magnetic disk, an optical disk, a solid-state drives, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage may store one or more programs and/or instructions to perform exemplary methods described in the present disclosure.

The I/O may input and/or output signals, data, information, etc. In some embodiments, the I/O may enable a user interaction with the processing engine 140. In some embodiments, the I/O may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port may be connected to a network (e.g., the network 120) to facilitate data communications. The communication port may establish connections between the processing engine 140 and the scanner 110, the terminal(s) 130, and/or the storage 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or a combination thereof. In some embodiments, the communication port may be and/or include a standardized communication port, such as RS232, RS485, etc. In some embodiments, the communication port may be a specially designed communication port. For example, the communication port may be designed in accordance with the digital imaging and communications in medicine (DICOM) protocol.

Figure 10:
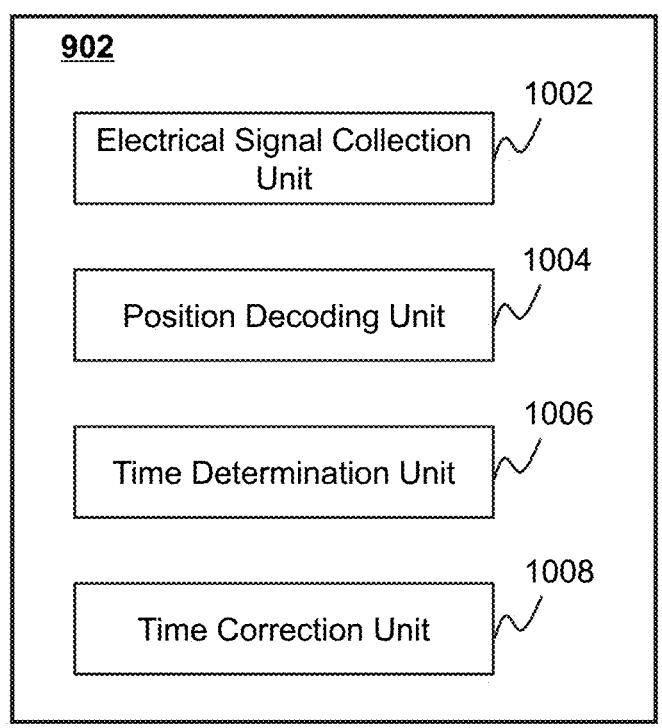
FIG. 10 is a schematic diagram illustrating an exemplary acquisition module according to some embodiments of the present disclosure.

FIG. 10 is a schematic diagram illustrating an exemplary acquisition module 902 according to some embodiments of the present disclosure. The acquisition module 902 may include an electrical signal collection unit 1002, a position decoding unit 1004, a time determination unit 1006, and a time correction unit 1008.

The electrical signal collection unit 1002 may collect electrical signals generated by the detector assembly 112 or a portion thereof (e.g., the photosensor array 220). In some embodiments, the electrical signal collection unit 1002 may be implemented by one or more ADCs. The electrical signal collection unit 1002 may digitize the electrical signals. In some embodiments, the electrical signal collection unit 1002 may collect electrical signals at a certain frequency. The frequency may be at a Hertz (Hz) level, an MHz level, 1000 MHz level, or any level thereof.

The position decoding unit 1004 may identify information relating to an interaction position of a radiation ray (e.g., γ ray) impinging on the scintillator array 210. The information relating to the interaction position may include a two-dimensional position (x, y) in the X-Y plane where the impinging radiation ray (e.g., γ ray) interacts with the scintillator array 210. More descriptions of the two-dimensional position (x, y) may be found elsewhere in the present disclosure. See, for example, FIGS. 12A-12C and the description thereof. The position decoding unit 1004 may identify a scintillator within the scintillator array 210 that has interacted with the impinging radiation ray based on the two-dimensional position. The information relating to the interaction position may further include a depth of interaction of the impinging radiation ray in the identified scintillator. In some embodiments, the position decoding unit 1004 may determine a depth of interaction of the impinging radiation ray. The position decoding unit 1004 may identify the information relating to the interaction position base on the electrical signals collected by the electrical signal collection unit 1002. It should be noted that in some embodiments, the position decoding unit 1004 may be configured in the electronics module 910.

The time determination unit 1006 may determine an interaction time when the impinging radiation ray interacts with the identified scintillator. The time determination unit 1006 may determine the interaction time based on the electrical signals collected by the electrical signal collection unit 1002. More descriptions of the time determination unit 1006 may be found elsewhere in the present disclosure. See, for example, FIG. 13 and the description thereof.

The time correction unit 1008 may correct the interaction time determined by the time determination unit 1006. In some embodiments, the time correction unit 1008 may correct the interaction time based on the depth of interaction. In some embodiments, the time correction unit 1008 may correct the interaction time based on one or more time correction techniques (e.g., time walk correction). In some embodiments, the time correction unit 1008 may be configured in the electronics module 910 to correct the interaction time based on the depth of interaction of an impinging radiation ray. More descriptions of the time correction unit 1008 may be found elsewhere in the present disclosure. See, for example, FIG. 14 and the description thereof.

In some embodiments, the interaction time determined by the time determination unit 1006 or corrected by the time correction unit 1008 may be used for determining a time of flight of the impinging radiation ray. In some embodiments, the processing module 906 may generate one or more lines of response (LORs) in PET imaging based on the information relating to the interaction position and the interaction time. The term "interaction position" and the term "hit position" are used interchangeably in the present disclosure. The term "interaction time" and the term "hit time" are used interchangeably in the present disclosure. In some embodiments, the depth of interaction may be used for improving the accuracy of a line of response (LOR). In some embodiments, the processing module 906 may further reconstruct an image based on the line(s) of response (LOR).

Figure 11:
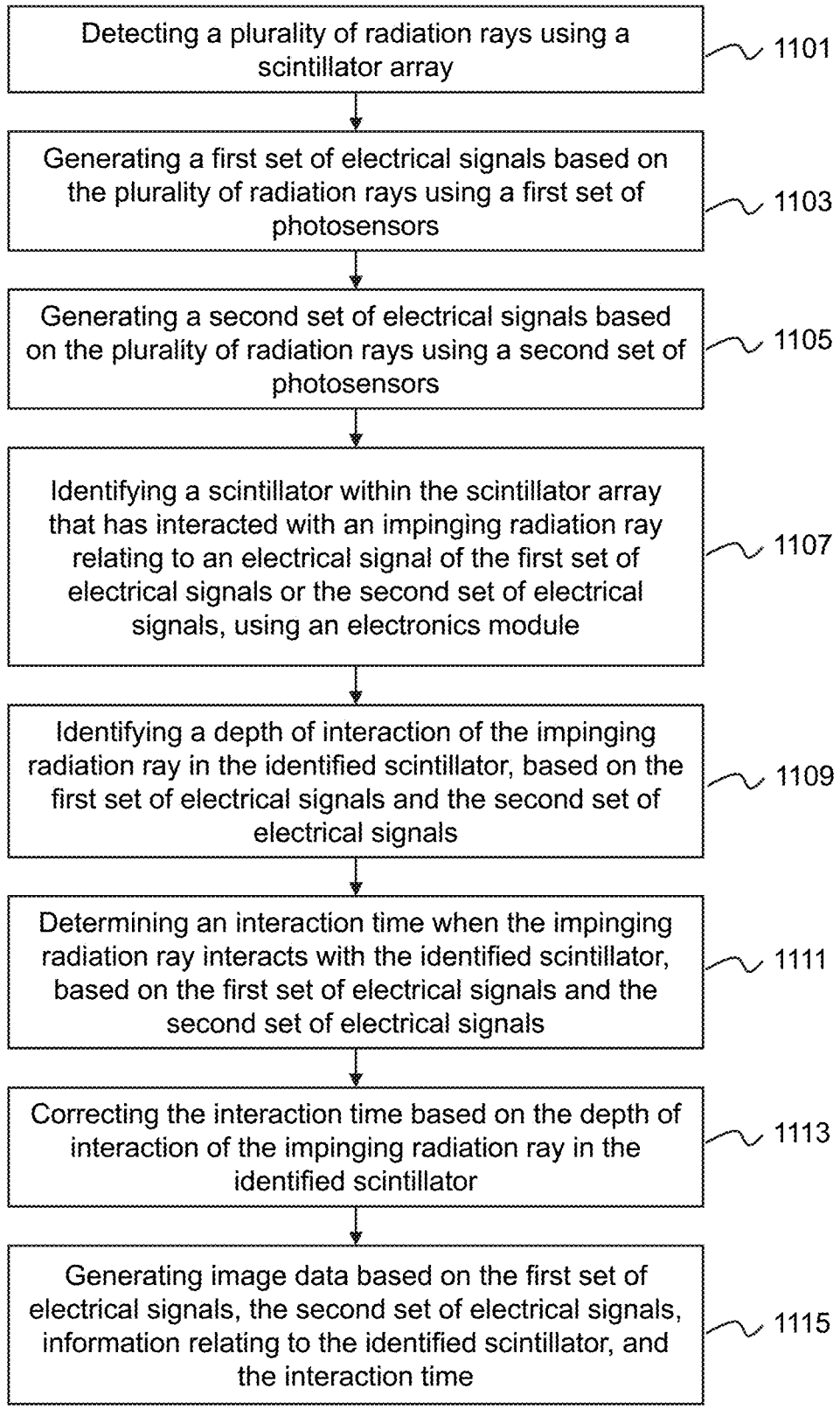
FIG. 11 is a flowchart illustrating an exemplary process for PET imaging according to some embodiments of the present disclosure.

FIG. 11 is a flowchart illustrating an exemplary process 1100 for PET imaging according to some embodiments of the present disclosure. At least a portion of the process 1100 may be implemented on the scanner 110. At least a portion of the process 1100 may be implemented on a computing device. For example, the process 1100 illustrated in FIG. 11 may be stored in the storage device 150 in the form of instructions, and invoked and/or executed by the processing engine 140.

In 1101, a plurality of radiation rays may be detected using a scintillator array. A plurality of radiation rays may impinge on a scintillator array (e.g., the scintillator array 210 shown in FIGS. 2-8E). The radiation rays may be γ rays that emit from a subject in the detection region 113. Before scanning, a radioactive tracer isotope may be injected into the subject. One or more atoms of the tracer isotope may be chemically incorporated into one or more biologically active molecules in the subject. The active molecules may become concentrated in one or more tissues of interest within the subject. The subject may be positioned on the table 114 and moved into the detection region 113 to make the tissue(s) of interest positioned in a field of view (FOV) of the scanner 110. The tracer isotope may undergo positron emission decay and emit one or more positrons. A positron may travel a short distance (e.g., about 1 mm) within a tissue of interest, lose kinetic energy and interact with an electron of the subject. The positron and the electron may annihilate and produce a pair of annihilation photons. The pair of annihilation photons (or radiation rays) may move in approximately opposite directions. A plurality of radiation rays may reach the detector assembly 112 and impinge on the scintillator array 210. Then, the scintillator array 210 may absorb the energy of the radiation ray (e.g., γ ray) photon, and convert the absorbed energy into light.

In 1103, a first set of electrical signals may be generated based on the plurality of radiation rays detected in 1101 using a first set of photosensors. In some embodiments, the first set of electrical signals may be generated by a first photosensor array including a first set of photosensors (e.g., the first photosensor array 220*a*). The first photosensor array may be optically coupled to the scintillator array configured to detect impinging radiation rays. The first set of photosensors may convert light signal(s) (e.g., the light(s) output from the scintillator array) into the first set of electrical signals.

In 1105, a second set of electrical signals may be generated based on the plurality of radiation rays detected in 1101 using a second set of photosensors. In some embodiments, the second set of electrical signals may be generated by a second photosensor array including a second set of photosensors (e.g., the second photosensor array 220*b*). The second photosensor array may be optically coupled to the scintillator array configured to detect impinging radiation rays. In some embodiments, the second photosensor array may be optically coupled to the same scintillator array as the first photosensor array. The second set of photosensors may convert light signal(s) (e.g., the light(s) output from the scintillator array) into the second set of electrical signals.

The second photosensor array may be configured differently compared to the first photosensor array. As described elsewhere in the present disclosure, the first photosensor array 220*a* and the second photosensor array 220*b* may be arranged on different surfaces of the scintillator array 210. The orientation of the photosensors in the first photosensor array 220*a* may be different from the orientation of the photosensors in the second photosensor array 220*b*. The first photosensor array 220*a* may be optically coupled to the scintillator layer 210 in a manner different from the second photosensor array 220*b*. Due at least to the different configurations of the first photosensor array and the second photosensor array, the first set of electrical signals may include information different from the second set of electrical signals.

In 1107, a scintillator within the scintillator array that has interacted with an impinging radiation ray may be identified. In some embodiments, the impinging radiation ray may relate to an electrical signal of the first set of electrical signals and/or an electrical signal of the second set of electrical signals. For example, the electrical signal may be generated based on an impinging radiation ray. In some embodiments, the scintillator may be identified using an electronics module (e.g., the electronics module 910). The scintillator may be identified based on the first set of electrical signals generated in 1103 and the second set of electrical signals generated in 1105. The electronics module 910 may use an algorithm to determine a two-dimensional interaction position (e.g., a position (x, y) in the X-Y plane of the scintillator array 210) where the impinging radiation ray has interacted with the scintillator array 210. In some embodiments, a first position of the impinging radiation ray that has interacted with the scintillator array in the first direction may be determined based on a first set of electrical signals using the algorithm. In some embodiments, the first direction may correspond to an X axis direction, the first position of the impinging radiation ray may correspond to a position in the X axis direction, and then, a position of a first photosensor that generates an electrical signal with maximum energy of the first set of electrical signals in the X axis direction may be designated as the first position, or a position of an energy centroid of the first set of electrical signals in the X axis direction may be designated as the first position. In some embodiments, a second position of the impinging radiation ray that has interacted with the scintillator array in the second direction may be determined based on a second set of electrical signals using the algorithm. In some embodiments, the second direction may correspond to a Y axis direction, the second position of the impinging radiation ray may correspond to a position in the Y axis direction, and then, a position of a second photosensor that generates an electrical signal with maximum energy of the second set of electrical signals in the Y axis direction may be designated as the second position, or a position of an energy centroid of the second set of electrical signals in the Y axis direction may be designated as the second position. Then, the scintillator that has an interaction with the impinging radiation ray may be identified based on the two-dimensional interaction position (e.g., the first position and the second position). In some embodiments, the algorithm may include a centroid algorithm, the Anger-Logic algorithm, a maximum likelihood estimation algorithm, or a localization algorithm based on an artificial neural network model, or the like, or any combination thereof.

In 1109, a depth of interaction of the impinging radiation ray in the identified scintillator may be identified. The depth of interaction may be identified by an electronics module (e.g., the electronics module 910). In some embodiments, the depth of interaction may be identified based on the first set of electrical signals generated in 1103 and the second set of electrical signals generated in 1105. Similar to operation 1107, the electronics module 910 may use an algorithm to determine the depth of interaction. The algorithm may include a centroid algorithm, the Anger-Logic algorithm, a maximum likelihood estimation algorithm, or a localization algorithm based on an artificial neural network model, or the like, or any combination thereof. The algorithm used in 1109 may be the same as or different from that used in 1107. For example, a centroid algorithm may be used in 1107 and 1109. As another example, a centroid algorithm may be used in 1107, while a localization algorithm based on an artificial neural network model may be used in 1109, or vice versa. In some embodiments, the depth of interaction of the impinging radiation ray in the identified scintillator may correspond to a position in a Z axis direction that is perpendicular to the first direction and the second direction, and then, a proportional distribution coefficient may be determined based on a ratio of first energy relating to the first set of electrical signals to second energy relating to the first set of electrical signals and the second set of electrical signals, and the depth of interaction of the impinging radiation ray may be determined based on the proportional distribution coefficient. In some embodiments, the first energy may relate to a first sum of the first set of electrical signals, the second energy may relate to a second sum of the first set of electrical signals and the second set of electrical signals, and the first set of electrical signals and the second set of electrical signals may be converted by at least one analog-to-digital converter and processed by the position decoding unit 1004.

In 1111, an interaction time when the impinging radiation ray interacts with the identified scintillator may be determined. The interaction time may be determined by the time determination unit 1006. The interaction time may be determined based on the first set of electrical signals generated in 1103 and/or the second set of electrical signals generated in 1105. In some embodiments, the interaction time may be determined based on the energy and/or collection time of the electrical signals. In some embodiments, the interaction time when an impinging radiation ray interacts with the identified scintillator may be determined using a time-to-digital converter (TDC). In some embodiments, if the impinging radiation ray interacts with the scintillator array from the first surface of the scintillator array, then a third sum of the first set of electrical signals may be determined, and the interaction time may be determined based on the third sum of the first set of electrical signals using a lower limit detection (LLD) circuit, a constant fraction discriminator (CFD) circuit, and/or a time-to-digital converter (TDC). In some embodiments, if the impinging radiation ray interacts with the scintillator array from the second surface of the scintillator array, and then a fourth sum of the second set of electrical signals may be determined, and the interaction time may be determined based on the fourth sum of the second set of electrical signals using a lower limit detection (LLD) circuit, or a constant fraction discriminator (CFD) circuit, and a time-to-digital converter (TDC). More descriptions of the determination of the interaction time may be found elsewhere in the present disclosure. See, for example, FIG. 13 and the description thereof.

In 1113, the interaction time determined in 1111 may be corrected. The interaction time may be corrected by the time correction unit 1008. In some embodiments, the interaction time may be corrected based on the depth of interaction of the impinging radiation ray in the identified scintillator. In some embodiments, the interaction time may be corrected using a time correction technique, for example, time walk correction. More descriptions of the correction of the interaction time may be found elsewhere in the present disclosure. See, for example, FIG. 13 and the description thereof.

In 1115, image data may be generated. In some embodiments, the image data may be generated by the processing module 906. In some embodiments, the image data may be generated based on the first set of electrical signals generated in 1103, the second set of electrical signals generated in 1105, information relating to the identified scintillator (e.g., the scintillator identified in 1107, the depth of interaction identified in 1109, etc.), and/or the interaction time (e.g., the interaction time determined in 1111, the interaction time corrected in 1113, etc.). In some embodiments, the image data may include data relating to one or more lines of response (LORs). In some embodiments, one or more coincidence events may be determined based on the two-dimensional interaction positions and the interaction times of a plurality of impinging radiation rays. If two radiation rays impinge on and interact with two scintillators located on opposite sides of the detection region 113 within a certain time window (e.g., 1 ns, 2 ns, 5 ns, 10 ns, etc.), the two radiation rays may be determined to come from the same annihilation, and regarded as a coincidence event. As used herein, if a line linking two scintillators intercepts with a subject being scanned (or a portion of the subject), the two scintillators may be referred to as being located on opposite sides of the detection region 113. The coincidence event may be assigned to a line of response (LOR) joining the two relevant scintillators that detect the coincidence event. The coincidence events that are assigned to same lines of response (LORs) may be projected and image data may be generated.

It should be noted that the above description of the process 1100 is merely provided for the purpose of illustration, and not intended to limit the scope of the present disclosure. For persons having ordinary skills in the art, multiple variations and modifications may be made to the process 1100 under the teachings of the present disclosure. However, those variations and modifications do not depart from the scope of the present disclosure. For example, operations 1103 and 1105 may be implemented simultaneously or alternately. As another example, operation 1109 may be implemented before operation 1107. As still another example, operation 1111 may be implemented before 1107 and/or 1109. As a further example, operation 1113 may be omitted. As still a further example, an operation for reconstructing an image based on the image data generated in 1115 may be added in the process 1100. The reconstructed image may show a tracer distribution within the subject. In some embodiments, the scintillator array may further include S rows of blocks arranged in the first direction and T columns of blocks arranged in the second direction, wherein each block may include N rows of scintillators arranged in the first direction and M columns of scintillators arranged in the second direction, and then, a sum of S electrical signals generated by S photosensors that are optically coupled to the first surface of the scintillator array and arranged in a same column of the T columns of blocks may be designated as one of the first set of electrical signals, and a sum of T electrical signals generated by T photosensors that are optically coupled to the second surface of the scintillator array and arranged in a same row of the S rows of blocks may be designated as one of the second set of electrical signals. Therefore, the signal processing operation may be similar to process 1100.

Figure 12A:
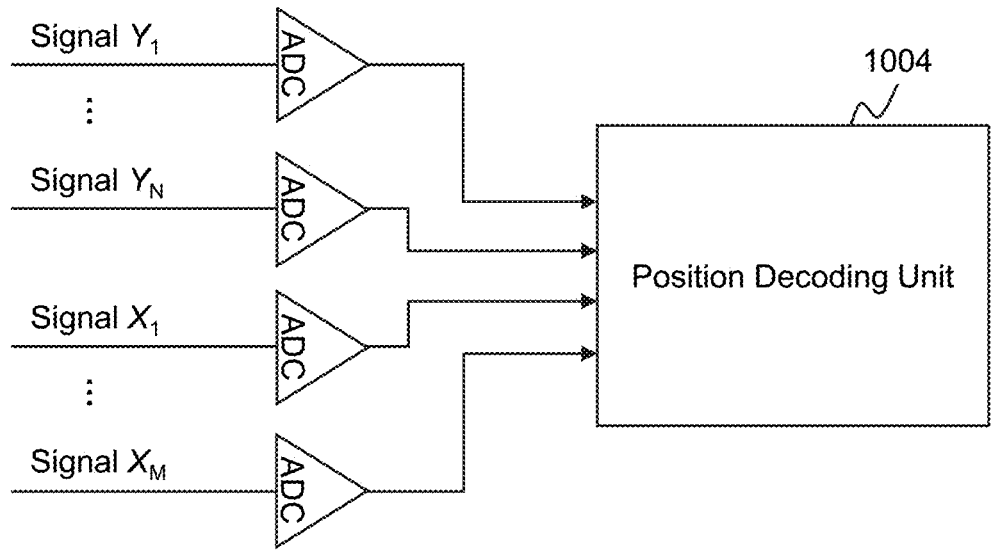
FIGS. 12A-12C are schematic diagrams illustrating exemplary electronics for determining information relating to the interaction position of a received radiation ray according to some embodiments of the present disclosure.
Figure 12B:
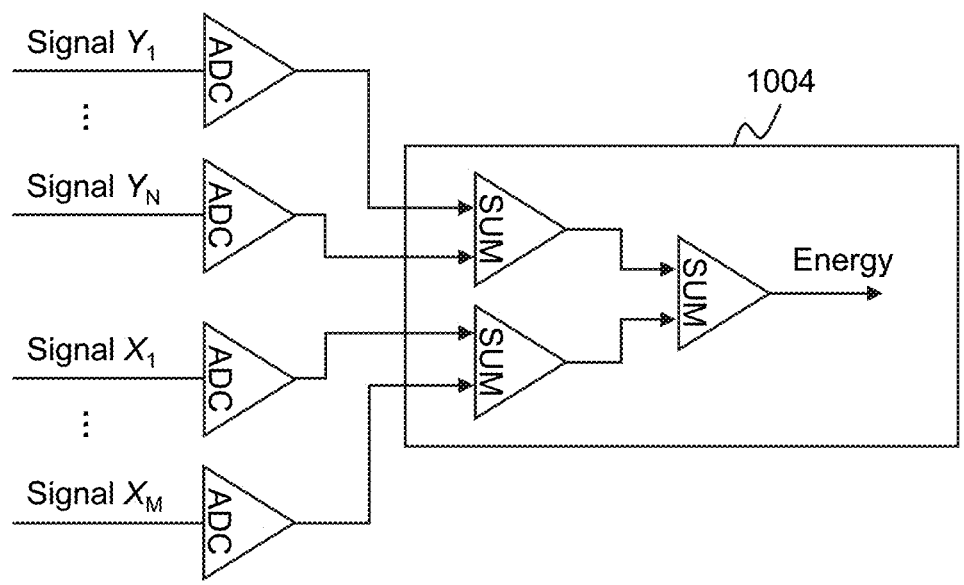
Figure 12C:
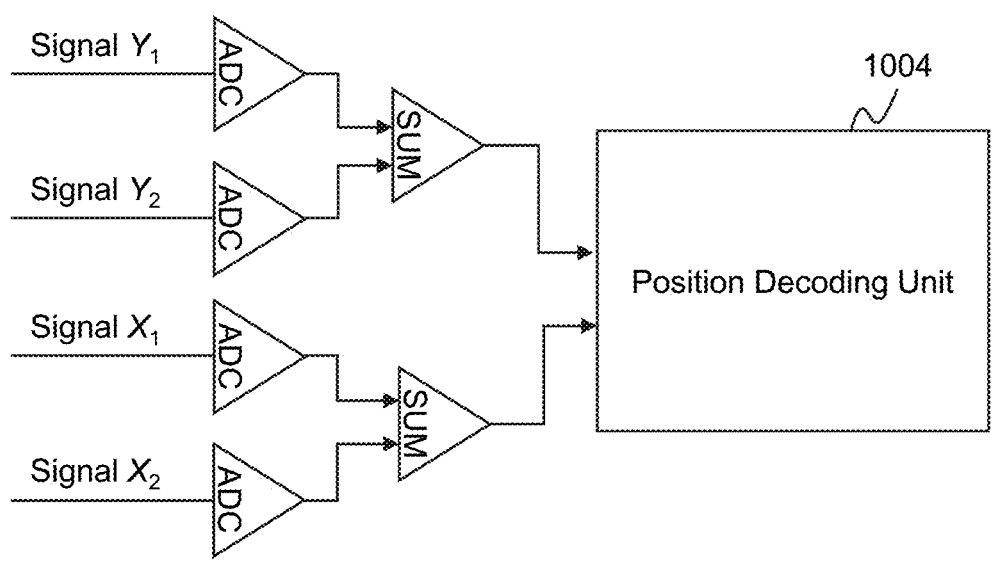

FIGS. 12A-12C are schematic diagrams illustrating exemplary electronics for determining information relating to the interaction position of a received radiation ray according to some embodiments of the present disclosure. The determination of the interaction position may be performed by the position decoding unit 1006. The interaction position of an impinging radiation ray (e.g., γ ray) may be determined based on one or more algorithms. The algorithm may include a centroid (i.e., center of gravity) algorithm, the Anger-Logic algorithm, a maximum likelihood estimation algorithm, a statistical-based localization algorithm, a three-dimensional nonlinear localization algorithm, a localization algorithm based on an artificial neural network model, or the like, or a combination thereof.

In some embodiments, the interaction position of an impinging radiation ray may be determined based on a first set of electrical signals (e.g., the signal the signal $Y_N'$ shown in FIG. 12A) and a second set of electrical signals (e.g., the signal $X_M'$, ..., the signal $X_M'$ shown in FIG. 12A). The first set of electrical signals may be generated by an N×1 first photosensor array 220a. The second set of electrical signals may be generated by a 1×M second photosensor array 220b. In some embodiments, the N×1 first photosensor array 220a may be arranged on a top surface of an N×M scintillator crystal array 210, and the 1×M second photosensor array 220b may be arranged on a bottom surface of the N×M scintillator array 210.

In some embodiments, a first electrical signal of the first set of electrical signals or a second electrical signal of the second set of electrical signals may include a pulse signal. The first electrical signal or the second electrical signal may including information regarding the energy of the impinging radiation ray. The first set of electrical signals (e.g., the signals $Y_1'$, ..., $Y_N'$ shown in FIG. 12A) and the second set of electrical signals (e.g., the signals $X_1'$, ..., $X_M'$ shown in FIG. 12A) may be transformed to digital signals by one or more analog-to-digital converters (ADC). Exemplary ADCs may include a flash ADC, a successive-approximation ADC, a ramp-compare ADC, a Wilkinson ADC, an integrating ADC, a delta-encoded ADC, a pipelined ADC, a sigma-delta ADC, a time-interleaved ADC, or the like, or a combination thereof. The ADC(s) may sample the electrical signals at a certain frequency. The frequency may be at the Hertz (Hz) level, the MHz level, the 1000 MHz level, etc. In some embodiments, an electrical signal may be sampled within a few nanoseconds, for example, ranging from one nanosecond to twenty nanoseconds. As shown in FIG. 12A, signal $Y_N'$ (N≥1) and signal $X_M'$ (M≥1) may be transformed into digital signals through an ADC connected to each of them. The digital signals may be transmitted to the position decoding unit 1004.

In some embodiments, the interaction position of a received radiation ray may be determined based on a centroid (i.e., center of gravity) algorithm. A center of gravity may be used to determine an average position of a mass. Merely by way of example, a two-dimensional interaction position (x, y) in the X-Y plane of the scintillator array 210 may be determined based on the following Equation (1) and Equation (2):

$$x = \frac{X_j}{\sum_{j=1}^{M} X_j}, \tag{1}$$

$$y = \frac{Y_i}{\sum_{i=1}^{N} Y_i}, \tag{2}$$

where x may be the coordinate position with respect to the X axis, y may be the coordinate position with respect to the Y axis, $X_j$ may be the energy represented by the digital signal $X_j$, and $Y_i$ may be the energy represented by the digital signal $Y_i$.

In some embodiments, a scintillator that has interacted with an impinging radiation ray may be identified based on the two-dimensional interaction position (x, y). In some embodiments, x may fall within one of a first range [0, $C_1$], a second range [$C_1$, $C_2$], ..., a jth range [$C_{j-1}$, 1], where $C_1$, $C_2$, ..., $C_{j-1}$ are preset coefficients. If x falls within the jth range, the scintillator may be identified to be in the jth column of the scintillator array 210. Similarly, y may fall within one of a first range [0, $D_1$], a second range [$D_1$, $D_2$], ..., an ith range [$D_{i-1}$, 1], where $D_1$, $D_2$, ..., $D_{i-1}$ are preset coefficients. If y falls within the ith range, the scintillator may be identified to be in the ith row of the scintillator array 210. Thus, the scintillator located at the ith row and the jth column may be identified to have a radiation ray interaction with the impinging radiation ray. In some embodiments, the preset coefficients $C_1$, $C_2$, ..., $C_{j-1}$, and $D_1$, $D_2$, ..., $D_{i-1}$ may be set based on a default or predetermined setting of the imaging system 100 or set by a user.

In some embodiments, the two-dimensional interaction position (x, y) may be determined based on a first maximum energy among the signal $Y_1$, ..., $Y_N$ and a second maximum energy among the signal $X_1$, ..., $X_M$. For example, if N equals 4 and M equals 4 (see the detector module 300 in FIG. 3A), eight signals $X_1$, $X_2$, $X_3$, $X_4$, $Y_1$, $Y_2$, $Y_3$, and $Y_4$ may be sampled. The first maximum energy $Y_{max}$ may be determined based on the signals $Y_1$, $Y_2$, $Y_3$, and $Y_4$. The second maximal energy $X_{max}$ may be determined based on the signals $X_1$, $X_2$, $X_3$, and $X_4$. If the photosensor that detects the first maximum energy $Y_{max}$ is $P_{Yi}$ (i=1, 2, 3, or 4), then the scintillator may be identified to be in the ith row of the scintillator array 210. If the photosensor that detects the second maximum energy $X_{max}$ is $P_{Xj}$ (j=1, 2, 3, or 4), then the scintillator may be identified to be in the jth column of the scintillator array 210. Thus, the scintillator located at the ith row and the jth column may be identified to have a radiation ray interaction with the received radiation ray. In some embodiments, the first maximum energy $Y_{max}$ may be determined based on a first comparator (not shown), and the second maximum energy $X_{max}$ may be determined based on a second comparator (not shown).

In some embodiments, a depth of interaction of the received radiation ray may be determined based on the centroid (i.e., center of gravity) algorithm. Merely by way of example, the depth of interaction may be determined based on the following Equation (3) or Equation (4):

$$z = \frac{\sum_{i=1}^{N} Y_i}{\sum_{i=1}^{N} Y_i + \sum_{j=1}^{M} X_j}, \qquad (3)$$

$$z = \frac{\sum_{i=1}^{N} X_j}{\sum_{i=1}^{N} Y_i + \sum_{j=1}^{M} X_j}, \qquad (4)$$

where z is the depth of interaction in the identified scintillator with respect to the Z axis. For example, if N equals 4 and M equals 4, eight signals $X_1, X_2, X_3, X_4, Y_1, Y_2, Y_3$, and $Y_4$ may be received. The depth of interaction of the received radiation ray may be determined based on Equation (5) or Equation (6):

$$z = \frac{X_1 + X_2 + X_3 + X_4}{X_1 + X_2 + X_3 + X_4 + Y_1 + Y_2 + Y_3 + Y_4}, \qquad (5)$$

$$z = \frac{Y_1 + Y_2 + Y_3 + Y_4}{X_1 + X_2 + X_3 + X_4 + Y_1 + Y_2 + Y_3 + Y_4}. \qquad (6)$$

In some embodiments, $\Sigma_{i=1}^{N}Y_i$ and/or $\Sigma_{j=1}^{M}X_j$ in Equations (3)-(6) may be determined by one or more adders (see SUM in FIG. 12B). For example, a first adder may be connected with the signals $Y_1', \ldots, Y_N'$ after they are digitized by corresponding ADCs to determine a sum of energies of the digital signals $Y_1, \ldots, Y_N$ (i.e., $\Sigma_{i=1}^{N}Y_i$). As another example, a second adder may be connected with the signals $X_1', \ldots, X_M'$ after they are digitized by corresponding ADCs to determine a sum of energies of the digital signals $X_1, \ldots, X_M$ (i.e., $\Sigma_{j=1}^{M}X_j$). As still another example, a third adder may be connected with the first adder and the second adder to determine a sum of energies of the digital signals $Y_1, \ldots, Y_N, X_1, \ldots, X_M$ (i.e., $\Sigma_{i=1}^{N}Y_i + \Sigma_{j=1}^{M}X_j$). The sum of energies and/or the individual signals may be transmitted to the position decoding unit 1004 for determining the interaction position. In some embodiments, as shown in FIG. 12B, the adders may be integrated in the position decoding unit 1004. In some embodiments, one or more of the adders may not be integrated in the position decoding unit 1004.

Merely by way of example, if N equals 2 and M equals 2 (see the detector module 600 in FIG. 6A), as shown in FIG. 12C, four digital signals $X_1, X_2, Y_1$ and $Y_2$ may be received. A two-dimensional interaction position (x, y) in the X-Y plane of the scintillator array 210 may be determined based on the following Equation (7) and Equation (8). In some embodiments, the two-dimensional interaction position (x, y) may be alternatively determined based on the following Equation (9) and Equation (10).

$$x = \frac{X_1}{X_1 + X_2}, \qquad (7)$$

$$y = \frac{Y_1}{Y_1 + Y_2}, \qquad (8)$$

$$x = \frac{X_2}{X_1 + X_2}, \qquad (9)$$

$$y = \frac{Y_2}{Y_1 + Y_2}. \qquad (10)$$

The depth of interaction may be determined based on the following Equation (11) or Equation (12):

$$z = \frac{X_1 + X_2}{X_1 + X_2 + Y_1 + Y_2}, \qquad (11)$$

$$z = \frac{Y_1 + Y_2}{X_1 + X_2 + Y_1 + Y_2}, \qquad (12)$$

As shown in FIG. 12C, a first adder may receive the signals $Y_1'$ and $Y_2'$ after they are digitized by corresponding ADCs to determine a sum of energies of the digital signals $Y_1$ and $Y_2$ (i.e., $Y_1+Y_2$ in Equations (8) and (10)-(12)). A second adder may receive the signals $X_1'$ and $X_2'$ after they are digitized by corresponding ADCs to determine a sum of energies of the digital signals $X_1$ and $X_2$ (i.e., $X_1+X_2$ in Equations (7), (9), (11), and (12)). The sum of energies and/or the individual signals may be transmitted to the position decoding unit 1004 for determining the interaction position. In some embodiments, the adders may be integrated into the position decoding unit 1004. In some embodiments, as shown in FIG. 12C, one or more of the adders may not be integrated into the position decoding unit 1004.

Figure 13:
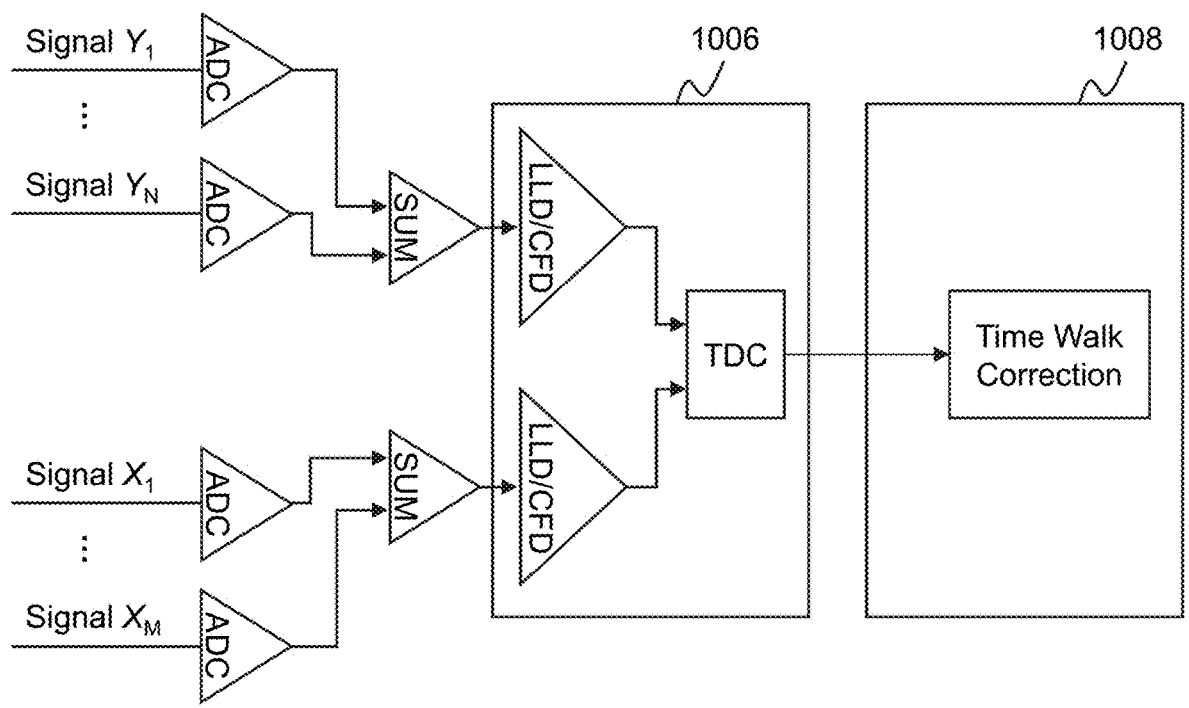
FIG. 13 is a schematic diagram illustrating exemplary electronics for determining information relating to the interaction time of a received radiation ray according to some embodiments of the present disclosure.

FIG. 13 is a schematic diagram illustrating exemplary electronics for determining information relating to the interaction time of a received radiation ray according to some embodiments of the present disclosure. The interaction time of an impinging radiation ray may be a time when a particle of the radiation ray interacts with an identified scintillator within the scintillator array 210. The determination of the interaction time may be performed by the time determination unit 1006. In some embodiments, as shown in FIG. 13, the interaction time may be determined based on a lower limit detection (LLD) circuit (or a constant fraction discriminator (CFD) circuit) and a time-to-digital converter (TDC).

In some embodiments, a first sum of energies of digital signals $Y_1, \ldots, Y_N$, and a second sum of energies of digital signals $X_1, \ldots, X_M$ may be compared with a first energy threshold and a second energy threshold, respectively. The first energy threshold and/or the second energy threshold may be 400 KeV, 500 KeV, 600 KeV, etc. In some embodiments, the first energy threshold may be the same as or different from the second energy threshold. If the first (or second) sum of energy is greater than the first (or second) energy threshold, the received radiation ray interaction with the scintillator array 210 may be determined to be a valid event. In some embodiments, whether the received radiation ray interaction is a valid event may be determined using a lower limit detection (LLD) circuit or a constant fraction discriminator (CFD) circuit.

If the interation of an impinging radiation ray with the identified scintillator is determined to be a valid event, then the digital signals $Y_1, \ldots, Y_N$, the digital signals $X_1, \ldots,$ $X_M$, the first sum of energies of digital signals $Y_1, \ldots, Y_N$, the second sum of energies of digital signals $X_1, \ldots, X_M$, and/or the sampling times of the signals may be transmitted to a time-to-digital converter (TDC) to determine the interaction time of the impinging radiation ray. The TDC may include an ASIC-based TDC, an FPGA-based TDC, or the like, or a combination thereof. The TDC may work based on a direct count technique, a Vernier technique, a tapped delay line technique, a difference delay chain technique, or the like, or a combination thereof.

In some embodiments, a time walk error may exist in the interaction time. In some embodiments, the interaction time may be corrected based on the depth of interaction and a time correction technique. The correction of the interaction time may be performed by the time correction unit 1008. The time correction technique may include a dead time correction, a time walk correction, etc. As shown in FIG. 13, a time walk correction may be used. In some embodiments, an initial timing ti of an electrical signal (e.g., the signal $Y_1', \ldots, Y_N', X_1', \ldots,$ or $X_M'$) may be determined based on a time-based readout (TBR) circuit. Then the time walk error may be corrected with a quantitative relationship between the ti and its signal amplitude. Description regarding the correction of the time walk error may be found in, for example, *Energy and Timing Measurement with Time-Based Detector Readout for PET Applications: Principle and Validation with Discrete Circuit Components* authored by Xishan Sun et al., which is hereby incorporated by reference.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and describe.

What is claimed is:

1. A PET system, comprising:
   a detector module configured to receive radiation rays and generate a plurality of light signals in response to the received radiation rays, the detector module comprising:
   a scintillator array having N rows of scintillators and M columns of scintillators, each row of scintillators being arranged in a first direction, each column of scintillators being arranged in a second direction;
   a first set of photosensors optically coupled to a first surface of the scintillator array, at least one photosensor of the first set of photosensors extending longitudinally in the second direction so as to be optically coupled to two or more scintillators in the second direction and being optically coupled to two or more columns of scintillators, wherein each scintillator in the scintillator array is optically coupled to only one photosensor of the first set of photosensors; and
   a second set of photosensors optically coupled to a second surface of the scintillator array, at least one photosensor of the second set of photosensors extending longitudinally in the first direction; and
   an electronics module coupled to the detector module and being configured to identify a scintillator within the scintillator array that has interacted with an impinging radiation ray.

2. The PET system of claim 1, wherein the first set of photosensors or the second set of photosensors include at least one silicon photomultiplier (SiPM).

3. The PET system of claim 1, further comprising a gantry with a detection region for receiving a subject to be scanned, wherein the first surface or the second surface of the scintillator array faces the detection region.

4. The PET system of claim 1, wherein the first direction is approximately perpendicular to the second direction.

5. The PET system of claim 1, wherein N equals M, or N is different from M.

6. The PET system of claim 1, wherein the electronics module is coupled to the first set of photosensors and the second set of photosensors, and the electronics module is further configured to:
   detect a first set of electrical signals generated by the first set of photosensors and a second set of electrical signals generated by the second set of photosensors, wherein the impinging radiation ray is relating to an electrical signal of the first set of electrical signals or the second set of electrical signals.

7. The PET system of claim 6, wherein the electronics module comprises:
   a plurality of analog-to-digital converters (ADC) configured to digitize the first set of electrical signals and the second set of electrical signals; and
   a processor configured to identify, based on the digitized first set of electrical signals and the digitized second set of electrical signals, the scintillator within the scintillator array that has interacted with the impinging radiation ray.

8. The PET system of claim 7, wherein the processor is further configured to determine a depth of interaction of the impinging radiation ray.

9. The PET system of claim 8, wherein the electronics module further comprises:
   a lower limit detection (LLD) circuit, or a constant fraction discriminator (CFD) circuit; and
   a time-to-digital converter (TDC) configured to determine an interaction time when the impinging radiation ray interacts with the identified scintillator.

10. The PET system of claim 9, wherein the processor is further configured to correct the interaction time based on the depth of interaction of the impinging radiation ray.

11. The PET system of claim 1, further comprising:
    a processing module configured to reconstruct an image based on the first set of electrical signals generated by the first set of photosensors and the second set of electrical signals generated by the second set of photosensors.

12. A method for PET imaging, comprising:
    detecting, using a scintillator array, a plurality of radiation rays, wherein the scintillator array includes N rows of scintillators and M columns of scintillators, each row of scintillators being arranged in a first direction, each column of scintillators being arranged in a second direction;
    generating, using a first set of photosensors, a first set of electrical signals based on the plurality of radiation rays, wherein the first set of photosensors are optically coupled to a first surface of the scintillator array, at least one photosensor of the first set of photosensors extending longitudinally in the second direction so as to be optically coupled to two or more scintillators in the second direction and being optically coupled to two or more columns of scintillators, wherein each scintillator in the scintillator array is optically coupled to only one photosensor of the first set of photosensors;

generating, using a second set of photosensors, a second set of electrical signals based on the plurality of radiation rays, wherein the second set of photosensors are optically coupled to a second surface of the scintillator array, at least one photosensor of the second set of photosensors extending longitudinally in the first direction; and identifying, using an electronics module, a scintillator within the scintillator array that has interacted with an impinging radiation ray relating to an electrical signal of the first set of electrical signals or the second set of electrical signals.

13. The method of claim 12, further comprising:
identifying a depth of interaction of the impinging radiation ray in the identified scintillator, based on the first set of electrical signals and the second set of electrical signals.

14. The method of claim 13, further comprising:
determining, using a time-to-digital converter (TDC), an interaction time when the impinging radiation ray interacts with the identified scintillator.

15. The method of claim 14, further comprising:
correcting the interaction time based on the depth of interaction of the impinging radiation ray in the identified scintillator.

16. The method of claim 13, wherein the depth of interaction of the impinging radiation ray in the identified scintillator corresponds to a position in a Z axis direction that is perpendicular to the first direction and the second direction, and wherein the identifying the depth of interaction of the impinging radiation ray in the identified scintillator comprises:

determining, based on a ratio of first energy relating to the first set of electrical signals to second energy relating to the first set of electrical signals and the second set of electrical signals, a proportional distribution coefficient; and determining, based on the proportional distribution coefficient, the depth of interaction of the impinging radiation ray.

17. The method of claim 16, wherein the first energy relates to a first sum of the first set of electrical signals, and the second energy relates to a second sum of the first set of electrical signals and the second set of electrical signals, and wherein the first set of electrical signals and the second set of electrical signals are converted by at least one analog-to-digital converter and processed by a processor.

18. The method of claim 14, wherein the impinging radiation ray interacts with the scintillator array from the second surface of the scintillator array, and wherein the determining an interaction time comprises:
determining a sum of the second set of electrical signals; and
determining, using a lower limit detection (LLD) circuit, or a constant fraction discriminator (CFD) circuit, and a time-to-digital converter (TDC), the interaction time based on the sum of the second set of electrical signals.

19. A detector module configured to receive radiation rays and generate a plurality of light signals in response to the received radiation rays, comprising:
a scintillator array having N rows of scintillators and M columns of scintillators, each row of scintillators being arranged in a first direction, each column of scintillators being arranged in a second direction;
a first set of photosensors optically coupled to a first surface of the scintillator array, at least one photosensor of the first set of photosensors extending longitudinally in the second direction so as to be optically coupled to two or more scintillators in the second direction and being optically coupled to two or more columns of scintillators, wherein each scintillator in the scintillator array is optically coupled to only one photosensor of the first set of photosensors; and
a second set of photosensors optically coupled to a second surface of the scintillator array, at least one photosensor of the second set of photosensors extending longitudinally in the first direction.

20. The detector module of claim 19, wherein each scintillator in the scintillator array is optically coupled to only one photosensor of the second set of photosensors.

* * * * *